United States Patent
Sumner et al.

(10) Patent No.: US 11,448,651 B2
(45) Date of Patent: Sep. 20, 2022

(54) MODIFYING BINDING MOLECULES TO MINIMIZE PRE-EXISITING INTERACTIONS

(71) Applicant: Regeneron Pharmaceuticals, Inc., Tarrytown, NY (US)

(72) Inventors: Giane Oliveira Sumner, Mahwah, NJ (US); Jihua Chen, Ossining, NY (US); Michael Partridge, Eastchester, NY (US); Albert Torri, Lagrangeville, NY (US); Manoj Rajadhyaksha, Colchester, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 412 days.

(21) Appl. No.: 16/507,880

(22) Filed: Jul. 10, 2019

(65) Prior Publication Data

US 2020/0018754 A1  Jan. 16, 2020

Related U.S. Application Data

(60) Provisional application No. 62/695,988, filed on Jul. 10, 2018.

(51) Int. Cl.
| | |
|---|---|
| *G01N 33/577* | (2006.01) |
| *C07K 16/28* | (2006.01) |
| *C07K 16/42* | (2006.01) |
| *G01N 33/53* | (2006.01) |

(52) U.S. Cl.
CPC ....... *G01N 33/577* (2013.01); *C07K 16/2866* (2013.01); *C07K 16/42* (2013.01); *G01N 33/5306* (2013.01); *C07K 2317/51* (2013.01); *C07K 2317/515* (2013.01); *C07K 2317/526* (2013.01); *C07K 2317/53* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,545,807 | A | 8/1996 | Surani et al. |
| 6,329,508 | B1 | 12/2001 | Friden |
| 6,596,541 | B2 | 7/2003 | Murphy et al. |
| 6,787,637 | B1 | 9/2004 | Schenk |
| 7,326,414 | B2 | 2/2008 | Bedian et al. |
| 8,048,421 | B2 | 11/2011 | Kai et al. |
| 8,541,564 | B2 | 9/2013 | Lillard, Jr. |
| 8,735,553 | B1 | 5/2014 | Li et al. |
| 9,139,653 | B1 | 9/2015 | Campbell et al. |
| 9,486,519 | B2 | 11/2016 | Sahin et al. |
| 2009/0074793 | A1 | 3/2009 | Martin et al. |
| 2011/0020840 | A1 | 1/2011 | Wolbink et al. |
| 2011/0212849 | A1 | 9/2011 | Verweij |
| 2017/0343560 | A1 | 11/2017 | Umana et al. |
| 2018/0092975 | A1 | 4/2018 | Chan et al. |

FOREIGN PATENT DOCUMENTS

| | | |
|---|---|---|
| CA | 2 967 602 A1 | 5/2016 |
| WO | WO 2004/108158 A1 | 12/2004 |
| WO | WO 2010/042904 A2 | 4/2010 |
| WO | WO 2010/122148 A1 | 10/2010 |
| WO | WO 2011/074965 A1 | 6/2011 |
| WO | WO 2014/138449 A1 | 9/2014 |
| WO | WO 2017/072210 A1 | 5/2017 |
| WO | WO 2018/091580 A1 | 5/2018 |
| WO | WO 2019/101863 A1 | 5/2019 |
| WO | WO 2020/014358 A1 | 1/2020 |
| WO | WO 2020/246891 A1 | 12/2020 |

OTHER PUBLICATIONS

Gunn et al. 'From the bench to clinical practice: understanding the challenges and uncertainties in immunogenicity testing for biopharmaceuticals.' Clinical and Experimental Immunology, 184: 137-146, 2016.*
Araujo et al., "Increased rheumatoid factor interference observed during immunogenicity assessment of an Fc-engineered therapeutic antibody," Journal of Pharmaceutical and Biomedical Analysis (2011) 55:1041-1049.
Bivi et al., "Investigation of pre-existing reactivity to biotherapeutics can uncover potential immunogenic epitopes and predict immunogenicity risk," mAbs, 2019, 10 pages, DOI: 10.1080/19420862.2019.1612699.
Chung et al., "Cetuximab-Induced Anaphylaxis and IgE Specific for Galactose-α-1,3-Galactose," N Engl J Med 2008;358:1109-1117.
Falkenburg et al., "Identification of Clinically and Pathophysiologically Relevant Rheumatoid Factor Epitopes by Engineered IgG Targets," Arthritis & Rheumatology, 2020, 72(12): 2005-2016 (12 pages).
Falkenburg et al., "Rheumatoid factors do not preferentially bind to ACPA-IgG or IgG with altered galactosylation," Rheumatology 2017, 56: 2025-2030.
Jefferis and Lefranc, "Human immunoglobulin allotypes Possible implications for immunogenicity," mAbs; Jul./Aug. 2009, 1:4, 1-7.
Kumar et al., "Mitigation of Pre-existing Antibodies to a Biotherapeutic in Non-clinical Species When Establishing Anti-drug Antibody Assay Cutpoint," The AAPS Journal, Jan. 2017, vol. 19, No. 1, pp. 313-319.
Rispens et al., "Antibodies to constant domains of therapeutic monoclonal antibodies: Anti-hinge antibodies in immunogenicity testing," Journal of Immunological Methods (2012) 375: 93-99.
Schneider et al., "An immunoinhibition approach to overcome the impact of pre-existing antibodies on cut point establishment for immunogenicity assessment of moxetumomab pasudotox," Journal of Immunological Methods (2016) 435: 68-76.

(Continued)

*Primary Examiner* — Nora M Rooney
(74) *Attorney, Agent, or Firm* — Cooley LLP; Ivor R. Elrifi; Matthew Pavao

(57) ABSTRACT

The present disclosure is directed towards modifying binding molecules in order to minimize pre-existing binding interactions, including binding molecules engineered to minimize or mitigate background reactivity in a sample matrix caused by drug non-specific binding interactions.

17 Claims, 10 Drawing Sheets

Specification includes a Sequence Listing.

(56) References Cited

OTHER PUBLICATIONS

Tatarewicz et al., "Rheumatoid factor interference in immunogenicity assays for human monoclonal antibody therapeutics," Journal of Immunological Methods (2010) 357:10-16.
Van Schie et al., "Cross-reactive and pre-existing antibodies to therapeutic antibodies—Effects on treatment and immunogenicity," mAbs, (2015) 7:4, 662-671.
Altschul et al., "Basic local alignment search tool," J. Mol. Biol. (1990) 215:403-410.
Altschul et al., "Gapped BLAST and PSI-BLAST: a new generation of protein database search programs," Nucleic Acids Res. (1997) 25(17):3389-3402.
Angal et al., "A single amino acid substitution abolishes the heterogeneity of chimeric mouse/human (IgG4) antibody," Molecular Immunology (1993) 30:105-108.
Bird et al., "Single-chain antigen-binding proteins," Science (1988) 242:423-426.
Falkenburg et al., "IgG Subclass Specificity Discriminates Restricted IgM Rheumatoid Factor Responses From More Mature Anti—Citrullinated Protein Antibody-Associated or Isotype-Switched IgA Responses," Arthritis & Rheumatology, Dec. 2015, vol. 67, No. 12, pp. 3124-3134.
GenBank Accession No. AAQ78418.1, Sequence 45 from U.S. Pat. No. 6,329,508, Sep. 12, 2003, 1 page.
GenBank Accession No. ABZ64885.1, Sequence 18 from U.S. Pat. No. 7,326,414, Feb. 7, 2008, 1 page.
GenBank Accession No. ABZ64895.1, Sequence 38 from U.S. Pat. No. 7,326,414, Feb. 7, 2008, 1 page.
GenBank Accession No. ABZ64897.1, Sequence 46 from U.S. Pat. No. 7,326,414, Feb. 7, 2008, 1 page.
GenBank Accession No. ABZ64907.1, Sequence 70 from U.S. Pat. No. 7,326,414, Feb. 7, 2008, 1 page.
GenBank Accession No. ABZ64913.1, Sequence 94 from U.S. Pat. No. 7,326,414, Feb. 7, 2008, 1 page.
GenBank Accession No. AER79058.1, Sequence 78 from U.S. Pat. No. 8,048,421, Nov. 3, 2011, 1 page.
GenBank Accession No. AGX48756.1, Sequence 70 from U.S. Pat. No. 8,541,564, Oct. 18, 2013, 1 page.
GenBank Accession No. AGX48757.1, Sequence 71 from U.S. Pat. No. 8,541,564, Oct. 18, 2013, 1 page.
GenBank Accession No. AGX48758.1, Sequence 72 from U.S. Pat. No. 8,541,564, Oct. 18, 2013, 1 page.
GenBank Accession No. AGX48762.1, Sequence 76 from U.S. Pat. No. 8,541,564, Oct. 18, 2013, 1 page.
GenBank Accession No. AGX48763.1, Sequence 77 from U.S. Pat. No. 8,541,564, Oct. 18, 2013, 1 page.
GenBank Accession No. AGX48764.1, Sequence 78 from U.S. Pat. No. 8,541,564, Oct. 18, 2013, 1 page.
GenBank Accession No. AJL58780.1, Sequence 87 from U.S. Pat. No. 8,735,553, Feb. 12, 2015, 1 page.
GenBank Accession No. AJL58781.1, Sequence 88 from U.S. Pat. No. 8,735,553, Feb. 12, 2015, 1 page.
GenBank Accession No. AOC11349.1, Sequence 126 from U.S. Pat. No. 9,139,653, Aug. 13, 2016, 1 page.
GenBank Accession No. ARI36266.1, Sequence 5 from U.S. Pat. No. 9,486,519, Apr. 13, 2017, 1 page.
Gonnet et al., "Exhaustive matching of the entire protein sequence database," Science (1992) 256:1443-1445.
Goodson, "Dental Applications," Medical Applications of Controlled Release, vol. 2, Chapter 6, 1984, pp. 115-138.
Green et al., "Antigen-specific human monoclonal antibodies from mice engineered with human Ig heavy and light chain YACs," Nature Genetics (1994) 7:13-21.
Holliger et al., ""Diabodies": Small bivalent and bispecific antibody fragments", Proc. Natl. Acad Sci. USA (1993) 90:6444-6448.
Huston et al., "Protein engineering of antibody binding sites: Recovery of specific activity in an anti-digoxin single-chain Fv analogue produced in *Escherichia coli*," Proc. Natl. Acad. Sci. USA (1988) 85:5879-5883.
Langer, "New methods of drug delivery," Science (1990) 249:1527-1533.
Lopez-Berestein, "Treatment of Systemic Fungal Infections with Liposomal-Amphotericin B," Liposomes in the Therapy of Infectious Disease and Cancer, Lopez-Berestein and Fidler (eds.), (1989) Liss, New York, pp. 317-327.
Pearson, "Using the FASTA program to search protein and DNA sequence databases," Methods Mol. Biol. (1994) 24: 307-331.
Powell et al., "Compendium of excipients for parenteral formulations" PDA J Pharm Sci Technol (1998) 52:238-311.
Sefton, "Implantable pumps," CRC Crit. Ref Biomed. Eng. (1987) 14:201-240.
Treat et al., "Liposome Encapsulated Doxorubicin Preliminary Results of Phase I and Phase II Trials," Liposomes in the Therapy of Infectious Disease and Cancer, Lopez-Berestein and Fidler (eds.), (1989) Liss, New York, pp. 353-365.
Ward et al., "Binding activities of a repertoire of single immunoglobulin variable domains secreted from *Escherichia coli*," Nature, Oct. 1989, 341:544-546.
Wu et al., "Receptor-mediated in Vitro Gene Transformation by a Soluble DNA Carrier System," J. Biol. Chem. (1987) 262(10):4429-4432.
Zhong et al., "Drug Target Interference in Immunogenicity Assays: Recommendations and Mitigation Strategies," The AAPS Journal, Nov. 2017, vol. 19, No. 6, pp. 1564-1575.
Bartelds, G.M. et al., "Development of Antidrug Antibodies Against Adalimumab and Association With Disease Activity and Treatment Failure During Long-term Follow-up," JAMA, 2011, 305(14): 1460-1468.
Carrasco-Triguero, M. et al., "Overcoming soluble target interference in an anti-therapeutic antibody screening assay for an antibody-drug conjugate therapeutic," Bioanalysis, 2012, 4(16): 2013-2026.
Casadevall, N. et al., "Pure red-cell aplasia and antierythropoietin antibodies in patients treated with recombinant erythropoietin," N Engl J Med, 2002. 346(7): pp. 469-475.
Chen, J. et al., "Overcoming multimeric target interference in a bridging immunogenicity assay with soluble target receptor, target immunodepletion and mild acidic assay pH," Bioanalysis, 2020, 12(15): 1071-1085.
Chen, J. et al., "Mitigating target interference in bridging immunogenicity assay with target-blocking reagents and mild basic pH," Bioanalysis, 2019, 11(17): 1569-1580.
Davies, A.M. et al., "Structural determinants of unique properties of human IgG4-Fc," Journal of Molecular Biology, 2014, 426: 630-644.
Devanarayan, V. et al., "Recommendations for Systematic Statistical Computation of Immunogenicity Cut Points," The AAPS Journal, 2017, 19(5): 1487-1498.
European Medicines Agency, "Guideline on Immunogenicity assessment of therapeutic proteins," European Medicines Agency, 2017, 24 pages.
Food and Drug Administration, HHS, "Draft Guidance for Industry on Immunogenicity Assessment for Therapeutic Protein Products," Federal Register, Feb. 2013, vol. 78, No. 28, pp. 9702-9703.
Franklin, E., et al., "An unusual protein component of high molecular weight in the serum of certain patients with rheumatoid arthritis," The Journal of Experimental Medicine, 1957, 105, pp. 425-438.
Hassanein, M., et al., "Assessment of clinically relevant immunogenicity for mAbs; are we over reporting ADA?" Bioanalysis, 2020, 12(18): 1325-1336.
Jefferis, "Aggregation, immune complexes and immunogenicity," mAbs, (2011) 3:6, 503-504.
Koren, E. et al., "Recommendations on risk-based strategies for detection and characterization of antibodies against biotechnology products," Journal of Immunological Methods, 2008, 333: 1-9.
Manno, C.S. et al., "Successful transduction of liver in hemophilia by AAV-Factor IX and limitations imposed by the host immune response," Nat Med, 2006. 12(3): p. 342-347, 592.
Michailidou, D., et al., "Allergic Aspects of IgG4-Related Disease: Implications for Pathogenesis and Therapy," Frontiers in Immunology, 2021, vol. 12, Article 693192, 12 pages.

(56) References Cited

OTHER PUBLICATIONS

Mire-Sluis, A.R. et al., "Recommendations for the design and optimization of immunoassays used in the detection of host antibodies against biotechnology products," J Immunol Methods, 2004,. 289: 1-16.

Monahan, P.E. et al., "Emerging Immunogenicity and Genotoxicity Considerations of Adeno-Associated Virus Vector Gene Therapy for Hemophilia," Journal of Clinical Medicine, 2021, 10, 2471, 24 pages.

Morris, A.L. et al., "Stereochemical Quality of Protein Structure Coordinates," Proteins: Structure, Function, and Bioinformatics, 1992, 12: 345-364.

Partridge, M.A. et al., "Bridging immunogenicity assays for IgG4 therapeutics: mitigating interference from Fc-Fc interactions," Bioanalysis, 2017, 9(9): 707-717.

Schuurman, J., et al., "The inter-heavy chain disulfide bonds of IgG4 are in equilibrium with intra-chain disulfide bonds," Molecular immunology, 2001, 38:1-8.

Shankar, G., et al., "Recommendations for the validation of immunoassays used for detection of host antibodies against biotechnology products," J Pharm Biomed Anal, 2008, 48:1267-1281.

Waaler, E., "On the occurrence of a factor in human serum activating the specific agglutination of sheep blood corpuscles," Acta Pathologica Microbiologica Scandinavica, 1940. 17(2): 172-188 https://doi.org/10.1111/j.1600-0463.2007.apm_682a.x.

Wang, L. et al., "Impact of pre-existing immunity on gene transfer to nonhuman primate liver with adeno-associated virus 8 vectors," Hum Gene Ther, 2011, 22(11): 1389-1401.

Xue and Rup, Evaluation of pre-existing antibody presence as a risk factor for posttreatment antidrug antibody induction: analysis of human clinical study data for multiple biotherapeutics. The AAPS Journal, 2013, 15(3): 893-896.

Xue, L. et al., "Pre-Existing Biotherapeutic-Reactive Antibodies: Survey Results Within the American Association of Pharmaceutical Scientists," The AAPS Journal, 2013, 15(3): 852-855.

Zhang, J. et al., "Immunogenicity assay cut point determination using nonparametric tolerance limit," Journal of Immunological Methods, 2017, 442: 29-34.

* cited by examiner

```
Human IgG1  LPAPIEKTISKAKGQPREPQVYTLPPSRDEL TKNQVSLTCLVKGFYPSDIAVEWESNGQPENNYKTTPPV
Human IgG2  LPAPIEKTISK TKGQPREPQVYTLPPSREEMTKNQVSLTCLVKGFYPSDIAVEWESNGQPENNYKTTPPM
Human IgG4  LPSS EKTISKAKGQPREPQVYTLPPSQEEMTKNQVSLTCLVKGFYPSDIAVEWESNGQPENNYKTTPPV Human IgG1  LDSDGSFFLYSKLTVDKSRWQQGNVFSCSVMHEALHNHYTQKSLSLSPGK       SEQ ID NO: 24
Human IgG2  LDSDGSFFLYSKLTVDKSRWQQGNVFSCSVMHEALHNHYTQKSLSLSPGK       SEQ ID NO: 25
Human IgG4  LDSDGSFFLYSR LTVDKSRWQ EGNVFSCSVMHEALHNHYTQKSLSLSLGK     SEQ ID NO: 26
```

Leucine 445 (L445) ←

FIG. 3

Minimizing Pre-existing Reactivity in Samples Using Alternate Forms of Labeled Drug in a Bridging Immunogenicity Assay.
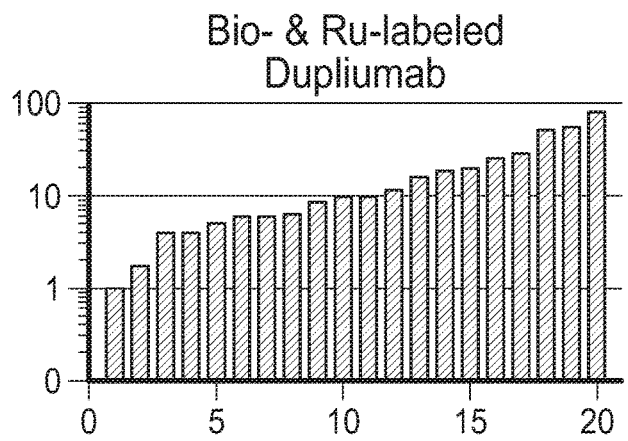
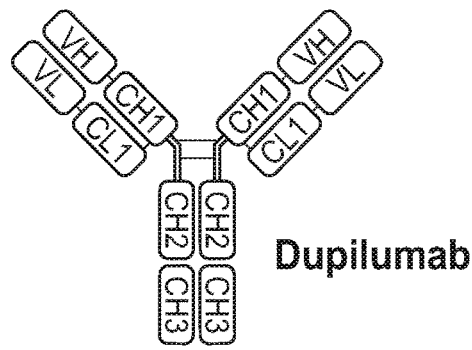
FIG. 6A
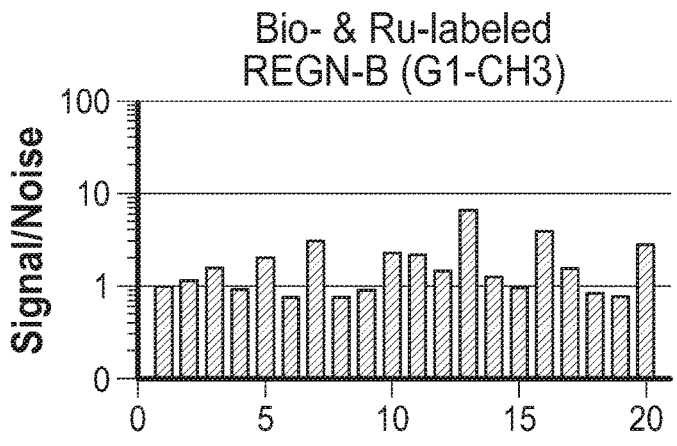
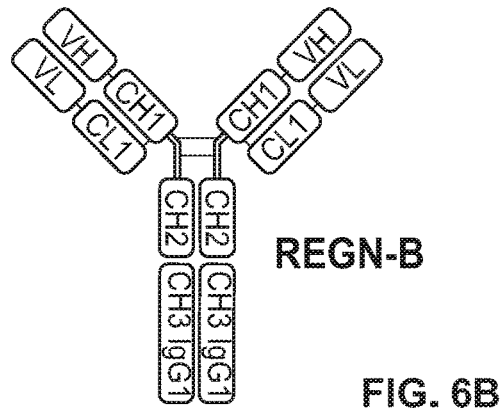
FIG. 6B
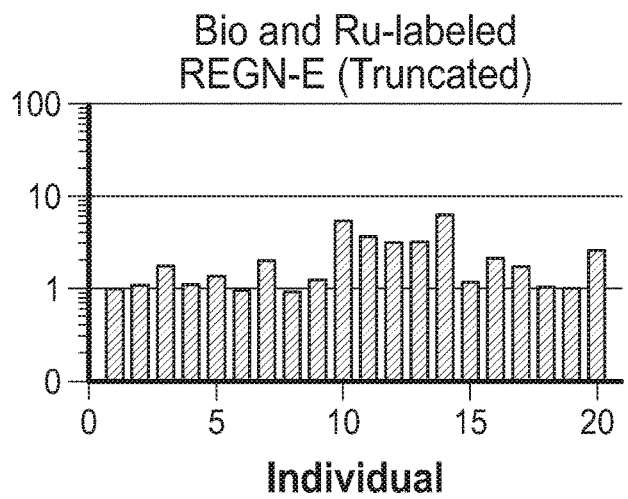
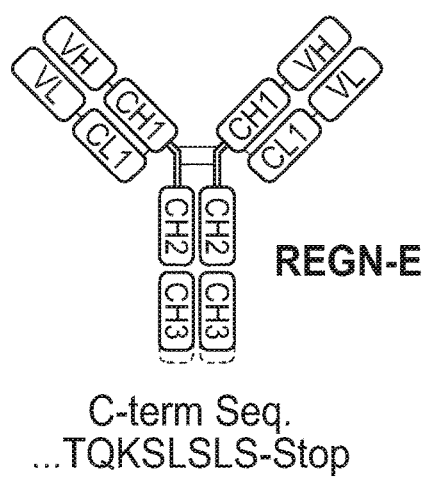
C-term Seq.
...TQKSLSLS-Stop
FIG. 6C

US 11,448,651 B2

MODIFYING BINDING MOLECULES TO MINIMIZE PRE-EXISITING INTERACTIONS

RELATED APPLICATIONS

This application claims priority to, and the benefit of, U.S. Provisional Application No. 62/695,988, filed on Jul. 10, 2018, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jul. 8, 2019, is named "REGE-004_SeqList.txt" and is 32,813 bytes in size.

FIELD OF THE DISCLOSURE

The present disclosure is directed towards modifying binding molecules in order to minimize pre-existing binding interactions, including binding molecules engineered to minimize or mitigate background reactivity in a sample matrix caused by drug non-specific binding interactions.

BACKGROUND

Biologic therapy is a valuable tool for eliminating, supplementing, or replacing elements of a subject's immune system to treat disease. Foreign biological material has a potential to induce an immune response from the subject being treated. This immune response can be triggered by the administration of a biologic therapeutic. However, a subject may have elements of their serum proteins that produce a signal prior to introduction of a biologic thus creating a high background or noise level when tested in an anti-drug antibody (ADA) assay.

A standard assay employed during the development and surveillance of a biologic therapeutic is the anti-drug antibody (ADA) assay. This assay is used to detect whether a subject's immune system has produced antibodies against an administered biologic. In order to have an effective assay the signal to noise ratio has to be such that meaningful data can be obtained and analyzed. In certain subjects, there already exists a high background (noise) even without the administration of any biologic such that detection of true treatment-emergent ADA is obfuscated due to the background signal and an effective ADA assay is attenuated.

The compositions and methods of the present invention provide a path towards reducing or eliminating the drug non-specific, pre-existing background reactivity present in some human serum or plasma samples that is observed in some ADA assays. It should also be understood that this drug non-specific binding may or may not interfere with the ability of a therapeutic to be active or remain in circulation.

SUMMARY

The present disclosure is directed to binding molecules engineered to mitigate drug non-specific pre-existing background reactivity in a subject sample either prior to or following the administration of the same. The instant invention is directed towards modifying binding molecules in order to minimize pre-existing binding interactions, including binding molecules engineered to minimize or mitigate background reactivity in a sample matrix caused by drug non-specific binding interactions.

The present disclosure further provides binding molecules specific for one or more particular targets. In one aspect, the disclosure is directed to binding molecules specific for IL4Rα (Interleukin 4 alpha) or IL13R (Interleukin 13). In another aspect, the disclosure provides binding molecules directed to IgG4 antibodies, or fragments thereof. A binding molecule as understood herein is a molecule that specifically interacts with a particular target. Examples of such binding molecules include, but are not limited to, antibodies (including monoclonal antibodies) and fragments thereof, engineered antibodies, fusion proteins, and other like antigen-binding molecules well-known to those skilled in the art. In one aspect, the target is IL4Rα. In another aspect of the present invention a non-naturally occurring binding molecule comprising a C-terminal heavy chain sequence LSPG (SEQ ID NO: 21) or an antigen-binding portion thereof is disclosed which is engineered to minimize or mitigate background reactivity in a sample matrix caused by drug non-specific binding interactions.

The instant disclosure provides a non-naturally occurring binding molecule, comprising a C-terminal heavy chain sequence SEQ ID NO: 21, or antigen-binding portion thereof, wherein said binding molecule mitigates interaction with pre-existing serum proteins and as such reduces high background signal during ADA analysis.

In certain embodiments of the present invention, the binding molecule comprises a CH domain sequence selected from the group consisting of SEQ ID NO: 5, SEQ ID NO: 6, SEQ ID NO: 7, and SEQ ID NO: 8, or an antigen-binding portion thereof. In certain embodiments, the binding molecule comprises a CH domain sequence selected from the group consisting of SEQ ID NO: 7 and SEQ ID NO: 8, or an antigen-binding portion thereof. In certain embodiments, the binding molecule comprises a CH domain comprising the amino acid sequence of SEQ ID NO: 7.

In certain embodiments of the present invention, the binding molecule comprises a truncated CH domain (REGN-E), wherein the sequence is SEQ ID NO: 22.

In certain embodiments of the non-naturally occurring binding molecule of the disclosure, the binding molecule comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14, and a $C_H3$ domain selected from the group consisting of: SEQ ID NO: 5, SEQ ID NO: 6, and SEQ ID NO: 7.

In certain embodiments of the invention, the binding molecule comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14, and a $C_H3$ domain comprising the amino acid sequence of SEQ ID NO: 21.

The disclosure provides a non-naturally occurring binding molecule, wherein the binding molecule comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14, and a $C_H3$ domain comprising the amino acid sequence of SEQ ID NO: 5, or SEQ ID NO: 6, or SEQ ID NO: 7, or SEQ ID NO: 21, or SEQ ID NO: 22.

In certain embodiments of the present invention, the binding molecule comprises a heavy chain variable region comprising the amino acid sequence of SEQ ID NO: 15, and a light chain variable region comprising the amino acid sequence of SEQ ID NO: 16.

In certain embodiments of the instant invention, the binding molecule comprises an IgG4 $C_H1$ region comprising the amino acid sequence of SEQ ID NO: 1.

In certain embodiments of the invention, the binding molecule comprises an IgG4 $C_H2$ region comprising the amino acid sequence of SEQ ID NO: 2.

In certain embodiments of the non-naturally occurring binding molecule of the disclosure, the binding molecule comprises a hinge region. In certain embodiments, the hinge region comprises the sequence of APEFLG (SEQ ID NO: 17).

In certain embodiments of the non-naturally occurring binding molecule of the disclosure, the binding molecule comprises an IgG4 constant region comprising the amino acid sequence of SEQ ID NO: 8.

The disclosure provides an assay comprising (a) a solid support, wherein a first component is operably-linked to the solid support; (b) at least one capture agent, wherein a second component is operably-linked to the at least one capture agent, wherein the capture agent comprises a first non-naturally occurring binding molecule such as a monoclonal antibody, wherein the first non-naturally occurring binding molecule such as a monoclonal antibody comprises a sequence encoding a $V_H$ CDR1 region, a sequence encoding a $V_H$ CDR2 region, a sequence encoding a $V_H$ CDR3 region, a sequence encoding a $V_L$ CDR1 region, a sequence encoding a $V_L$ CDR2 region, a sequence encoding a $V_L$ CDR3 region, and a sequence encoding a heavy chain constant region, wherein the heavy chain constant region comprises the sequence SEQ ID NO: 21, and (c) at least one detection agent, wherein a detectable label is operably-linked to the detection agent, wherein the detection agent comprises a second non-naturally occurring binding molecule such as a monoclonal antibody, wherein the sequence encoding the detection agent comprises the sequence encoding a $V_H$ CDR1 region, the sequence encoding a $V_H$ CDR2 region, the sequence encoding a $V_H$ CDR3 region, the sequence encoding the $V_L$ CDR1 region, the sequence encoding a $V_L$ CDR2 region, the sequence encoding a $V_L$ CDR3 region of the first non-naturally occurring binding molecule of (b), and wherein the first component and the second component selectively bind to one another.

In certain embodiments of the assays disclosed, the first non-naturally occurring binding molecule comprises a sequence encoding a heavy chain variable region and a sequence encoding a light chain variable region and wherein the second non-naturally occurring binding molecule comprises the sequence encoding a heavy chain variable region and the sequence encoding a light chain variable region of the first non-naturally occurring binding molecule.

In certain embodiments of the assays disclosed, the first non-naturally occurring binding molecule comprises a sequence encoding a heavy chain constant region comprising SEQ ID NO: 7.

In certain embodiments of the assays disclosed, the first non-naturally occurring binding molecule comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14.

In certain embodiments of the assays disclosed, the first non-naturally occurring binding molecule comprises a heavy chain variable region comprising the amino acid sequence SEQ ID NO: 15, and a light chain variable region comprising the amino acid sequence SEQ ID NO: 16.

In one embodiment of the present invention, the $C_H3$ domain of an IgG4 antibody such as dupilumab is switched for an IgG1 $C_H3$ domain. In still a further embodiment, the $C_H3$ domain of an IgG4 antibody like dupilumab is truncated. In one aspect, the truncation occurs at Serine 444.

In certain embodiments of the assays disclosed, the detection agent comprises dupilumab. In certain embodiments, the second non-naturally occurring binding molecule comprises dupilumab.

In certain embodiments of the assays disclosed, the first component comprises streptavidin. In certain embodiments, the second component comprises biotin.

The disclosure provides an assay comprising (a) a solid support, wherein a first component is operably-linked to the solid support; (b) at least one capture agent, wherein a second component is operably-linked to the at least one capture agent and wherein the capture agent comprises the non-naturally occurring binding molecule of the disclosure or a composition of the disclosure; and (c) at least one detection agent, wherein a detectable label is operably-linked to the detection agent and wherein the detection agent comprises dupilumab; wherein the first component and the second component selectively bind to one another. In certain embodiments, the first component comprises streptavidin. In certain embodiments, the second component comprises biotin. In certain embodiments, a binding molecule that does not specifically bind to a sequence of a variable region of dupilumab, does not bind the at least one capture agent. In certain embodiments, a binding molecule that specifically binds to a sequence of a variable region of dupilumab, binds to the at least one capture agent and to the at least one detection agent.

The disclosure provides a method of determining a level of immunogenicity of a biologic therapy in a subject, comprising (a) contacting a biological sample from the subject with the assay of the disclosure under conditions suitable to allow binding of at least one binding molecule in the biological sample with the at least one capture agent and to the at least one detection agent, wherein the subject has been administered the binding molecule therapy prior to the contacting step, (b) detecting a signal from the at least one detection agent, and (c) identifying the level of immunogenicity of the subject as high when the signal from (b) is above a threshold value or (d) identifying the level of immunogenicity of the subject as low when the signal from (b) is below the threshold value.

Certain embodiments of the present invention are directed toward methods for determining a level of immunogenicity of a biologic therapy, wherein the biologic therapy comprises a binding molecule described herein. In one aspect, the biologic comprises dupilumab.

In particular embodiments of the present invention, methods for determining a level of immunogenicity of a biologic therapy are disclosed, wherein the threshold is a predetermined value. In certain aspects, the threshold is a safety threshold.

In certain embodiments of the instant invention, the amount of the biologic therapy is a therapeutically-effective dose, wherein a therapeutically-effective dose is an amount of therapeutic agent, e.g. a binding molecule of the present invention, that when administered to a subject is of sufficient quantity to achieve an intended purpose.

In some embodiments of the present invention, the level of immunogenicity is a baseline level. In certain aspects, the level of immunogenicity is a subsequent or post treatment level.

In other embodiments of the present invention, the subject is a participant in a clinical trial. In one aspect, the subject is a patient undergoing a medical treatment. In another aspect, the medical treatment is beginning and the level of immunogenicity is a baseline level. In yet another aspect, the medical treatment is ongoing and the level of immunogenicity is a subsequent level. In still another aspect, the medical treatment is ending and the level of immunogenicity is a final level. In another aspect, the subject is a healthy individual.

In still other embodiments of the instant invention, the subject has an inflammatory disease or disorder, an autoimmune disease or disorder, an allergic disease or disorder, an immune disease or disorder, or a benign proliferative disease or disorder. In one aspect, the subject has atopic dermatitis, asthma, allergic rhinitis, allergic conjunctivitis, eosinophilic esophagitis, nasal polyps, ABPA (Allergic bronchopulmonary aspergillosis), Bullous Pemphigoid, Chronic Obstructive pulmonary disease (COPD), HFE (Hand and foot eczema), Prurigo Nodularis, or any Type 2 inflammatory response or a combination thereof. The subject can have any disease or medical condition.

The present disclosure provides a non-naturally occurring monoclonal antibody comprising a C-terminal heavy chain sequence comprising a sequence selected from the group consisting of SEQ ID NO: 7 and SEQ ID NO: 13, or an antigen-binding portion thereof. A C-terminal heavy chain sequence can be a $C_H3$ domain sequence. A C-terminal heavy chain sequence can comprise SEQ ID NO: 7. A C-terminal heavy chain sequence can comprise SEQ ID NO: 13. A C-terminal heavy chain sequence can comprise a CH domain sequence comprising SEQ ID NO: 8. A C-terminal heavy chain sequence can comprise a CH domain sequence comprising SEQ ID NO: 22.

A non-naturally occurring monoclonal antibody comprising a $C_H3$ domain consisting of a sequence selected from the group consisting of SEQ ID NO: 7 and SEQ ID NO: 13, or an antigen-binding portion thereof.

A non-naturally occurring monoclonal antibody comprising C-terminal heavy chain sequence consisting of a sequence selected from the group consisting of SEQ ID NO: 8 and SEQ ID NO: 22, or an antigen-binding portion thereof.

A non-naturally occurring monoclonal antibody, wherein the antibody comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14, and a $C_H3$ domain consisting of an amino acid sequence selected from the group consisting of SEQ ID NO: 5, SEQ ID NO: 6, SEQ ID NO: 7 and SEQ ID NO: 13, or an antigen-binding portion thereof.

The preceding antibodies can further comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14.

The present disclosure provides a non-naturally occurring monoclonal antibody, wherein the antibody comprises a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14, and a $C_H3$ domain comprising the amino acid sequence selected from the group consisting of SEQ ID NO: 5, SEQ ID NO: 6, SEQ ID NO: 7 and SEQ ID NO: 13, or an antigen-binding portion thereof.

The preceding antibodies can comprise a heavy chain variable region comprising the amino acid sequence of SEQ ID NO: 15, and a light chain variable region comprising the amino acid sequence of SEQ ID NO: 16, or an antigen-binding portion thereof. The preceding antibodies can comprise an IgG4 $C_H1$ region comprising the amino acid sequence of SEQ ID NO: 1. The preceding antibodies can comprise an IgG4 $C_H2$ region comprising the amino acid sequence of SEQ ID NO: 2. An IgG4 $C_H2$ region can comprise a hinge region. A hinge region can comprise the sequence of APEFLG (SEQ ID NO: 17).

The antibodies of the present disclosure can mitigate high background signal during an immunogenicity analysis.

The present disclosure provides an assay comprising: (a) a solid support, wherein a first component is operably-linked to the solid support; (b) at least one capture agent, wherein a second component is operably-linked to the at least one capture agent, wherein the capture agent comprises a first non-naturally occurring monoclonal antibody of the present disclosure, and (c) at least one detection agent, wherein a detectable label is operably-linked to the detection agent, wherein the detection agent comprises a second non-naturally occurring monoclonal antibody of the present disclosure, and wherein the first component and the second component selectively bind to one another.

A detection agent can comprise dupilumab. A second non-naturally occurring monoclonal antibody can comprise dupilumab. A first component can comprise streptavidin. A second component can comprise biotin.

The present disclosure provides an assay comprising: (a) a solid support, wherein a first component is operably-linked to the solid support; (b) at least one capture agent, wherein a second component is operably-linked to the at least one capture agent and wherein the capture agent comprises the non-naturally occurring monoclonal antibody of the present disclosure; and (c) at least one detection agent, wherein a detectable label is operably-linked to the detection agent and wherein the detection agent comprises dupilumab; wherein the first component and the second component selectively bind to one another. A first component can comprise streptavidin.

A second component can comprise biotin.

In some aspects, an at least one capture agent does not bind an antibody that does not specifically bind to a sequence of a variable region of dupilumab. In some aspects, an at least one capture agent and the at least one detection agent binds to an antibody that specifically binds to a sequence of a variable region of dupilumab.

The present disclosure provides a method of determining a level of immunogenicity of a monoclonal antibody therapy in a subject, comprising: (a) contacting a biological sample from the subject with the any assay of the present disclosure under conditions suitable to allow binding of at least one antibody in the biological sample with the at least one capture agent and to the at least one detection agent, wherein the subject has been administered the monoclonal antibody therapy prior to the contacting step; (b) detecting a signal from the at least one detection agent; and (c) identifying the level of immunogenicity of the subject as high when the signal from (b) is above a threshold value; or (d) identifying the level of immunogenicity of the subject as low when the signal from (b) is below the threshold value.

A monoclonal antibody therapy can comprise an antibody of the present disclosure.

A monoclonal antibody therapy can comprise dupilumab. A threshold can be a predetermined value. A threshold can be a safety threshold. An amount of the monoclonal antibody therapy can be a therapeutically-effective dose. A level of immunogenicity can be a baseline level. A level of immunogenicity can be a subsequent level.

A subject can be a participant in a clinical trial. A subject can be a patient undergoing a medical treatment. A medical treatment can be beginning and a level of immunogenicity can be a baseline level. A medical treatment can be ongoing and a level of immunogenicity can be a subsequent level. A medical treatment can be ending and a level of immunogenicity can be a final level. A subject can be a healthy individual. A subject can have an inflammatory disease or disorder, an autoimmune disease or disorder, an allergic disease or disorder, an immune disease or disorder, or a benign proliferative disease or disorder. A subject can have atopic dermatitis, asthma, allergic rhinitis, allergic conjunctivitis, eosinophilic esophagitis, nasal polyps or a combination thereof.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

BRIEF DESCRIPTION OF THE DRAWINGS

FIG. 3 is a drawing showing a diagrammatic representation of the amino acid sequence alignment and comparison of the $C_H3$ domain of the wild type IgG4, IgG1 and IgG2 subtypes. The Leucine at position 445 is the third from the C terminal end of the $C_H3$ domain sequence, as indicated by the arrow.

FIG. 6A is a plot showing assay signal from a subset of patient baseline samples using a drug specific bridging anti-drug antibody (ADA) assay, similar to that described in FIG. 4, with intact dupliumab employed as the capture and detection reagents.

FIG. 6B is a plot showing assay signal from the same subset of patient baseline samples tested in FIG. 6A, using a revised bridging ADA assay with REGN-B (FIG. 2, a human IgG4 mAb where the entire $C_H3$ of IgG4 was switched to an IgG1 $C_H3$ domain) as the capture and detection reagents.

FIG. 6C is a plot showing assay signal from the same subset of patient baseline samples tested in FIG. 6A, using a revised bridging ADA assay with REGN-E (FIG. 2, a human IgG4 mAb where the $C_H3$ domain is truncated with a stop codon after Serine 444) as the capture and detection reagents.

DETAILED DESCRIPTION

Figure 1:
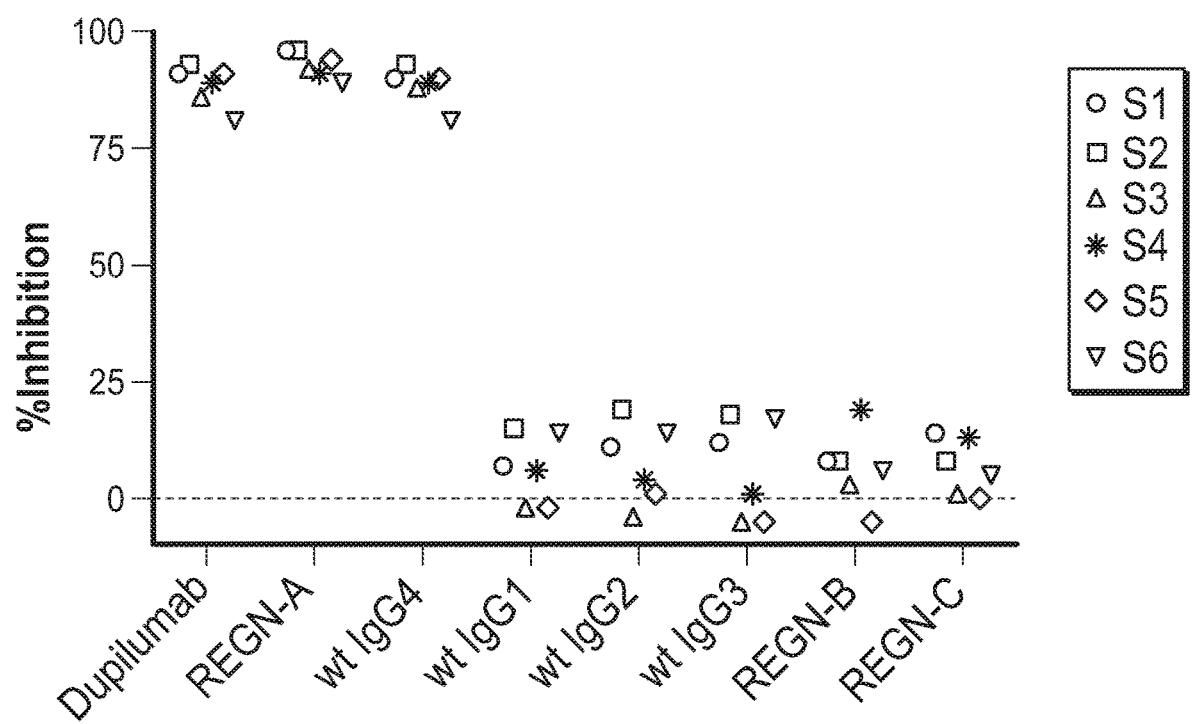
FIG. 1 is a plot characterizing the specificity of pre-existing reactivity in baseline patient samples using competitive antibody constructs in an anti-drug antibody (ADA) assay. On the y-axis, percent inhibition from 0 to 100 in increments of 25. On the X-axis, the specific competitive antibody construct used in the bridging assay, listed from left to right: dupilumab, REGN-A, wt IgG4, wt IgG1, wt IgG2, wt IgG3, REGN-B and REGN-C. The six patient samples (S1-S6) are represented, in order, as a circle, a square, a triangle point up, an asterisk, a diamond, and a triangle point down. Antibody reagents mentioned in the graph were used at 200 µg/mL as competitive inhibitors in the ADA confirmation assay format. High percent inhibition in the assay indicates that the given competitor was able to inhibit the pre-existing signals in these samples, suggesting that the competitor molecule contains a region to which the pre-existing reactivity binds. Lower percent inhibitions indicate that the competitor molecule does not contain a region to which the pre-existing reactivity can bind.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The term "human IL4R" (hIL-4R), as used herein, is intended to refer to a human cytokine receptor that specifically binds interleukin-4 (IL-4), IL-4Rα (SEQ ID NO: 18). The term "human interleukin-13" (hIL-13) refers to a cytokine that specifically binds IL-13 receptor, and "hIL-13/hIL-13R1 complex" refers to the complex formed by hIL-13 binding to hIL-13R1 complex, which complex binds hIL-4 receptor to initiate biological activity.

The term "binding molecule," as used herein is intended to refer to molecules that specifically interact with and bind to a particular target. The target can comprise a biologic or small (chemical) molecule. The target molecule may define an antigen or antigenic moiety. Examples of a binding molecule include, but are not limited to, antibodies (including monoclonal antibodies, bispecific antibodies, as well as antibody fragments), fusion proteins, and other antigen-binding molecule known to those skilled in the art.

The term "antibody," as used herein, is an example of a binding molecule and refers to as an immunoglobulin that typically comprises four polypeptide chains, two heavy (H) chains and two light (L) chains inter-connected by disulfide bonds. Each heavy chain comprises a heavy chain variable region (HCVR or $V_H$) and a heavy chain constant region. The heavy chain constant region comprises three domains, $C_H1$, $C_H2$ and $C_H3$. Each light chain comprises a light chain variable region (LCVR or $V_L$) and a light chain constant region. The light chain constant region comprises one domain (CL1). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Antibodies can include antibodies in the IgG1, IgG2, IgG3 or IgG4 subclasses. Antibodies can also comprise a combination of regions from different subclasses. IgG4 antibodies can include, but are not limited to, dupilumab and cemiplimab.

Other examples of "binding molecules" include, but are not limited to, bi-specific antibodies, tri-specific antibodies, tetra-specific antibodies and penta-specific antibodies. In some aspects, the bi-specific antibodies, tri-specific antibodies, tetra-specific antibodies and penta-specific antibodies can comprise an Fc portion of an antibody. In some aspects, the bi-specific antibodies, tri-specific antibodies, tetra-specific antibodies, penta-specific antibodies can comprise an IgG4 backbone. Another example of a "binding molecule" is an antibody-drug conjugate (ADC). In some aspects, an ADC can comprise an IgG4 backbone. Another example of a "binding molecule" is a Bi-specific T-cell engager (BiTE). In some aspects the BiTE can comprise an IgG4 backbone. Another example of a "binding molecule" is a TRAP fusion protein. In some aspects, the TRAP fusion protein has an IgG4 backbone. Another example of a "binding molecule" is a fynomer.

The term "antigen-binding portion" of an antibody (or simply "antibody portion" or "antibody fragment"), as used herein, refers to one or more fragments of an antibody that retain the ability to specifically bind to an antigen (e.g., hIL-4Rα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the $V_L$, $V_H$, $C_L1$ and $C_H1$ domains; (ii) a F(ab')2 fragment, a bivalent fragment comprising two F(ab)' fragments linked by a disulfide bridge at the hinge region; (iii) a Fc fragment comprising the $V_H$ and $C_H1$ domains; (iv) a Fv fragment comprising the $V_L$ and $V_H$ domains of a single arm of an antibody, (v) a dAb fragment (Ward et al. (1989) Nature 241:544-546), which comprises a $V_H$ domain; and (vi) a CDR. Furthermore, although the two domains of the Fv fragment, $V_L$ and $V_H$, are coded for by separate genes, they can be joined, using recombinant methods, by a synthetic linker that enables them to be made as a single contiguous chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883. Such single chain antibodies are also intended to be encompassed within the term "antigen-binding portion" of an antibody. Other forms of single chain antibodies, such as diabodies, are also encompassed (see e.g., Holliger et al. (1993) Proc. Natl. Acad Sci. USA 90:6444-6448).

A "neutralizing" or "blocking" antibody, as used herein, is intended to refer to an antibody whose binding to hIL-4Rα results in inhibition of the biological activity of hIL-4 and/or hIL-13. This inhibition of the biological activity of hIL-4 and/or IL-13 can be assessed by measuring one or more indicators of hIL-4 and/or hIL-13 biological activity known to the art, such as hIL-4- and/or IL-13-induced cellular activation and hIL-4 binding to hIL-4Rα (see examples below).

A "CDR" or complementarity determining region is a region of hypervariability interspersed within regions that are more conserved, termed "framework regions" (FR). In different embodiments of the anti-hIL-4Rα antibody or fragment of the disclosure, the FRs may be identical to the human germline sequences or may be naturally or artificially modified.

The term "epitope" is an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "immunogenicity" refers to the ability of an antigen or immunogen to induce an immune response in the body of a human or an animal. Protein therapeutics have the ability to provoke adverse immune responses that can interfere with drug pharmacokinetics and efficacy. This immune response can take the form of the production of anti-drug antibodies (ADAs).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Typically, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In certain embodiments, conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each of which is herein incorporated by reference.

Methods for generating human antibodies include those described in, for example, U.S. Pat. No. 6,596,541, Green et al. (1994) Nature Genetics 7:13-21), U.S. Pat. Nos. 5,545, 807, 6,787,637.

Rodents can be immunized by any method known in the art (see, for example, Harlow and Lane (1988) *Antibodies: A Laboratory Manual* 1988 Cold Spring Harbor Laboratory; Malik and Lillehoj (1994) Antibody Techniques, Academic Press, CA). Antibodies of the disclosure are typically prepared with the use of VELOCIMMUNE® technology (U.S. Pat. No. 6,596,541). A transgenic mouse in which the endogenous immunoglobulin heavy and light chain variable regions are replaced with the corresponding human variable regions is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable regions of the light and heavy chains may be isolated directly from antigen-specific lymphocytes.

The DNA encoding the variable regions of the heavy and light chains of the antibody may be isolated and operably linked to DNA encoding the human heavy and light chain constant regions. The DNA may be then expressed in a cell capable of expressing the fully human antibody. In a specific embodiment, the cell is a CHO cell.

Antibodies may be therapeutically useful in blocking a ligand-receptor interaction or inhibiting receptor component interaction, rather than by killing cells through fixation of complement (complement-dependent cytotoxicity) (CDC) and participation antibody-dependent cell-mediated cytotoxicity (ADCC). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

Human immunoglobulins can exist in two forms that are associated with hinge heterogeneity. In one form, an immunoglobulin molecule comprises a stable four-chain construct of approximately 150-160 kDa in which the dimers are held together by an interchain heavy chain disulfide bond. In a second form, the dimers are not linked via interchain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. (1993) Molecular Immunology 30: 105) to levels typically observed using a human IgG1 hinge. The instant disclosure encompasses antibodies having one or more mutations in the hinge, $C_H2$ or $C_H3$ region that may be desirable, for example, in production, to improve the yield of the desired antibody form.

Initially, high affinity chimeric antibodies are isolated having a human variable region and a mouse constant region. As described below, the antibodies are characterized and selected for desirable characteristics, including binding affinity to hIL-4Rα, ability to block hIL-4 binding to hIL-4Rα, and/or selectivity for the human protein. The mouse constant regions are replaced with desired human constant regions to generate the fully human antibodies of the disclosure, for example wild-type or modified IgG4 or IgG1 (for example, SEQ ID NO: 4, 19, 20 and 23). While the constant region selected may vary according to specific use, high affinity antigen-binding and target specificity characteristics reside in the variable region.

Immunogenicity Assays

The present disclosure provides a non-naturally occurring binding molecule such as a monoclonal antibody, or antigen-binding portion thereof, comprising a C-terminal heavy chain sequence LSPG (SEQ ID NO: 21). In certain embodiments, the C-terminal heavy chain is a human $C_H3$ domain. In certain embodiments, the human IgG is of the IgG4 class. In certain embodiments, the heavy chain sequence comprises SEQ ID NO: 7. In certain embodiments, the heavy chain sequence comprises SEQ ID NO: 8.

The disclosure provides immunogenicity assays comprising an anti-IL-4Rα binding molecule such as an antibody or antigen-binding fragments thereof of the present disclosure. Immunogenicity assays of the disclosure can take the form of anti-drug antibody (ADA) assays. ADA assays of the disclosure may be ADA bridging assays or direct enzyme-linked immunosorbent (ELISA) assays. In an ADA bridging assay, a biotinylated form of the binding molecule in question is bound to streptavidin on a plate. Binding molecules like antibodies present in the sample then bind to both the biotinylated binding molecule and a labeled form of the same binding molecule, forming a bridging interaction with a detectable signal from the label. Suitable labels will be known to one ordinarily skilled in the art. Exemplary labels comprise Ruthenium, horseradish peroxidase, alkaline phosphatase and fluorophores. The ADA bridging assay may include titration of the sample performing the bridging reaction to generate a standard curve, and the use of a cold, unlabeled competitor antibody to inhibit the reaction.

Figure 4:
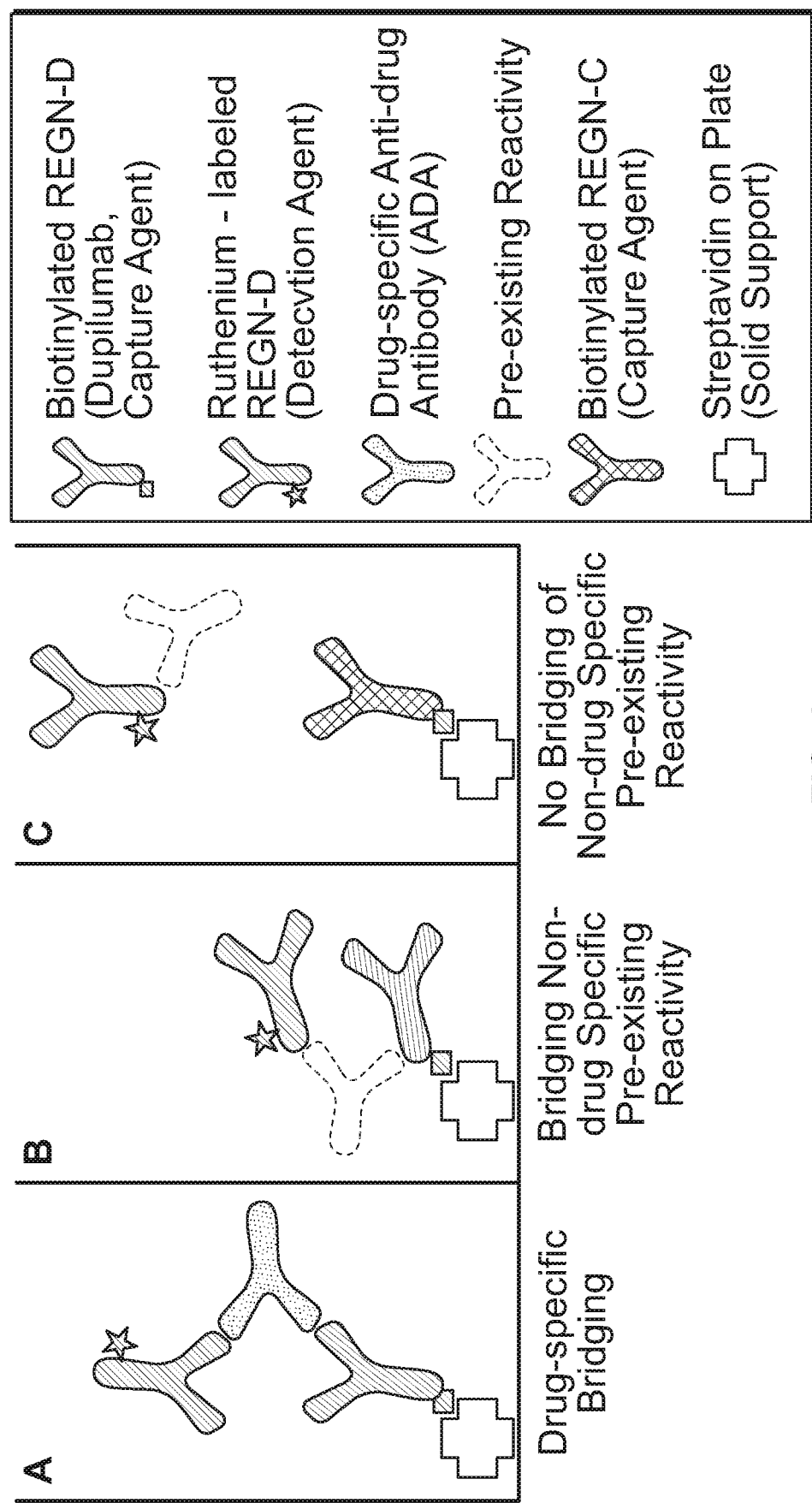
FIG. 4 is one embodiment illustrating a diagrammatic representation of a drug specific bridging (panel A, ADA assay #1), non-drug specific bridging due to pre-existing reactivity in the current ADA assay (panel B) and no non-drug specific bridging due to use of REGN-C as the capture agent (panel C, ADA assay #2). Streptavidin on the plate is shown as a gray cross, the biotin moiety as a small black square and the Ruthenium label as a star. The biotinylated REGN-D (dupilumab) capture agent (black forked structure) is shown in panels A and B, while in panel C, biotinylated REGN-C is shown (black and white checkered forked structure). Pre-existing reactivity is represented in panels B and C as a smaller dashed outlined forked structure.

FIG. 4 illustrates a drug specific bridging ADA assay in Panel A; in Panel B, a non-drug specific bridging assay due to pre-existing reactivity in the current ADA assay; and no non-drug specific bridging ADA assay due to use of REGN-C as the capture agent seen in Panel C. Pre-existing reactivity is represented in panels B and C as a smaller dashed outlined forked structure. It should be understood that for the disclosed embodiment assay reagent molecular analogs REGN-A, B, C, D and E are interchangeable thus permitting a skilled artisan to design various permutations of the assay as described. In one aspect, in order to reduce background a skilled artisan could combine REGN-D with any of the following reagents to form novel combinations: REGN-B, REGN-C or REGN-E (D+B, D+C, D+E or flipped such that B+D, C+D or E+D) such that the order of alignment is "capture agent"+"detection agent." In another aspect a skilled artisan could make the following pairs in order to reduce background signal: B+B, C+C or E+E.

In certain embodiments of the present disclosure, levels of immunogenicity (or ADA) are determined using binding molecules such antibodies (or antigen-binding portions thereof). In certain embodiments, the levels of immunogenicity are evaluated for dupilumab using an IgG4 antibody. One issue that typically needs to be addressed in these immunogenicity studies is the high background signal which is often associated with the IgG4 antibody used. In order to mitigate this high background, the present disclosure provides IgG4 antibodies comprising a heavy chain sequence of either SEQ ID NO: 21, SEQ ID NO: 22, SEQ ID NO: 7 or SEQ ID NO: 8 resulting in a lower background signal.

In certain embodiments of the present disclosure, a binding molecule such as an antibody, or antigen-binding portion thereof, comprises (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a $C_H3$ or CH sequence selected from the group consisting of SEQ ID NO: 21, SEQ ID NO: 22, SEQ ID NO: 7 and SEQ ID NO: 8, wherein the binding molecule exhibits reduced background reactivity in an immunogenicity (ADA) assay compared to a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a $C_H3$ or CH sequence not selected from the group consisting of SEQ ID NO: 21, SEQ ID NO: 22, SEQ ID NO: 7 and SEQ ID NO: 8. In certain embodiments, the CH domain sequence of (3) can include SEQ ID NO: 5 and SEQ ID NO: 6.

In one embodiment of the present invention, the $C_H3$ domain of an IgG4 antibody such as dupliumab is switched for an IgG1 $C_H3$ domain resulting in a lower background signal (FIG. 6B). In still a further embodiment, the $C_H3$ domain of an IgG4 antibody like dupliumab is truncated. In one aspect, the truncation occurs at Serine 444 resulting in a lower background signal (FIG. 6C).

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a $C_H3$ or CH sequence selected from the group consisting of SEQ ID NO: 21, SEQ ID NO: 22, SEQ ID NO:13, SEQ ID NO: 7 and SEQ ID NO: 8.

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a $C_H3$ or CH sequence, wherein the $C_H3$ or CH sequence comprises a one or more sequences selected from the group consisting of SEQ ID NO: 21, SEQ ID NO: 22, SEQ ID NO:13, SEQ ID NO: 7 and SEQ ID NO: 8.

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a $C_H3$ sequence, wherein the $C_H3$ sequence comprises one or more sequences selected from the group consisting of SEQ ID NO: 7, SEQ ID NO:13, or SEQ ID NO: 21.

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a CH sequence, wherein the CH sequence comprises one or more sequences selected from the group consisting of SEQ ID NO: 8, SEQ ID NO: 21 and SEQ ID NO: 22.

In some aspects, the present disclosure provides a binding molecule comprising a CH sequence, wherein the CH sequence comprises one or more sequences selected from the group consisting of SEQ ID NO: 8, SEQ ID NO: 21 and SEQ ID NO: 22.

In some aspects, the present disclosure provides a binding molecule comprising a $C_H3$ sequence, wherein the $C_H3$ sequence comprises one or more sequences selected from the group consisting of SEQ ID NO: 7, SEQ ID NO:13, or SEQ ID NO: 21.

In some aspects, the present disclosure provides a binding molecule comprising an IgG4 CH domain comprising a Proline to Leucine amino acid substitution at position 445.

In some aspects, the present disclosure provides a binding molecule comprising SEQ ID NO: 1, SEQ ID NO: 2 and SEQ ID NO: 5.

In some aspects, the present disclosure provides a binding molecule comprising SEQ ID NO: 1, SEQ ID NO: 2 and SEQ ID NO: 6.

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a CH sequence comprising SEQ ID NO: 1, SEQ ID NO: 2 and SEQ ID NO: 5.

In some aspects, the present disclosure provides a binding molecule comprising (1) one or more $V_L$ chain sequences selected from the group consisting of SEQ ID NO: 12, LGS, SEQ ID NO: 14 and combinations thereof, (2) one or more $V_H$ chain sequences selected from the group consisting of SEQ ID NO: 9, SEQ ID NO: 10, SEQ ID NO: 11 and combinations thereof, and (3) a CH sequence comprising SEQ ID NO: 1, SEQ ID NO: 2 and SEQ ID NO: 6.

In some aspects, the present disclosure provides a binding molecule comprising at least one polypeptide sequence with at least about 99% sequence identity to SEQ ID NO: 7. In some aspects, the present disclosure provides a binding molecule comprising at least one polypeptide sequence with at least about 98% sequence identity to SEQ ID NO: 7. In some aspects, the present disclosure provides a binding molecule comprising at least one polypeptide sequence with at least about 97% sequence identity to SEQ ID NO: 7. In some aspects, the present disclosure provides a binding molecule comprising at least one polypeptide sequence with at least about 96% sequence identity to SEQ ID NO: 7. In some aspects, the present disclosure provides a binding molecule comprising at least one polypeptide sequence with at least about 95% sequence identity to SEQ ID NO: 7. In some aspects, the present disclosure provides a binding molecule comprising at least one polypeptide sequence with at least about 94% sequence identity to SEQ ID NO: 7. In some aspects, the present disclosure provides a binding molecule comprising at least one polypeptide sequence with at least about 93% sequence identity to SEQ ID NO: 7. In some aspects, the present disclosure provides a binding molecule comprising at least one polypeptide sequence with at least about 92% sequence identity to SEQ ID NO: 7. In some aspects, the present disclosure provides a binding molecule comprising at least one polypeptide sequence with at least about 91% sequence identity to SEQ ID NO: 7. In some aspects, the present disclosure provides a binding molecule comprising at least one polypeptide sequence with at least about 90% sequence identity to SEQ ID NO: 7.

In some aspects, the present disclosure provides a binding molecule comprising at least one polypeptide sequence with at least about 99% sequence identity to SEQ ID NO: 8. In some aspects, the present disclosure provides a binding molecule comprising at least one polypeptide sequence with at least about 98% sequence identity to SEQ ID NO: 8. In some aspects, the present disclosure provides a binding molecule comprising at least one polypeptide sequence with at least about 97% sequence identity to SEQ ID NO: 8. In some aspects, the present disclosure provides a binding molecule comprising at least one polypeptide sequence with at least about 96% sequence identity to SEQ ID NO: 8. In some aspects, the present disclosure provides a binding molecule comprising at least one polypeptide sequence with at least about 95% sequence identity to SEQ ID NO: 8. In some aspects, the present disclosure provides a binding molecule comprising at least one polypeptide sequence with at least about 94% sequence identity to SEQ ID NO: 8. In some aspects, the present disclosure provides a binding molecule comprising at least one polypeptide sequence with at least about 93% sequence identity to SEQ ID NO: 8. In some aspects, the present disclosure provides a binding molecule comprising at least one polypeptide sequence with at least about 92% sequence identity to SEQ ID NO: 8. In some aspects, the present disclosure provides a binding molecule comprising at least one polypeptide sequence with at least about 91% sequence identity to SEQ ID NO: 8. In some aspects, the present disclosure provides a binding molecule comprising at least one polypeptide sequence with at least about 90% sequence identity to SEQ ID NO: 8.

In some aspects, the present disclosure provides a binding molecule comprising at least one polypeptide sequence with at least about 99% sequence identity to SEQ ID NO: 13. In some aspects, the present disclosure provides a binding molecule comprising at least one polypeptide sequence with at least about 98% sequence identity to SEQ ID NO: 13. In some aspects, the present disclosure provides a binding molecule comprising at least one polypeptide sequence with at least about 913% sequence identity to SEQ ID NO: 13. In some aspects, the present disclosure provides a binding molecule comprising at least one polypeptide sequence with at least about 96% sequence identity to SEQ ID NO: 13. In some aspects, the present disclosure provides a binding molecule comprising at least one polypeptide sequence with at least about 95% sequence identity to SEQ ID NO: 13. In some aspects, the present disclosure provides a binding molecule comprising at least one polypeptide sequence with at least about 94% sequence identity to SEQ ID NO: 13. In some aspects, the present disclosure provides a binding molecule comprising at least one polypeptide sequence with at least about 93% sequence identity to SEQ ID NO: 13. In some aspects, the present disclosure provides a binding molecule comprising at least one polypeptide sequence with at least about 92% sequence identity to SEQ ID NO: 13. In some aspects, the present disclosure provides a binding molecule comprising at least one polypeptide sequence with at least about 91% sequence identity to SEQ ID NO: 13. In some aspects, the present disclosure provides a binding molecule comprising at least one polypeptide sequence with at least about 90% sequence identity to SEQ ID NO: 13.

In some aspects, the present disclosure provides a binding molecule comprising at least one polypeptide sequence with at least about 99% sequence identity to SEQ ID NO: 7, wherein the at least one polypeptide sequence comprises SEQ ID NO: 21. In some aspects, the present disclosure provides a binding molecule comprising at least one polypeptide sequence with at least about 98% sequence identity to SEQ ID NO: 7, wherein the at least one polypeptide sequence comprises SEQ ID NO: 21. In some aspects, the present disclosure provides a binding molecule comprising at least one polypeptide sequence with at least about 97% sequence identity to SEQ ID NO: 7, wherein the at least one polypeptide sequence comprises SEQ ID NO: 21. In some aspects, the present disclosure provides a binding molecule comprising at least one polypeptide sequence with at least about 96% sequence identity to SEQ ID NO: 7, wherein the at least one polypeptide sequence comprises SEQ ID NO: 21. In some aspects, the present disclosure provides a binding molecule comprising at least one polypeptide sequence with at least about 95% sequence identity to SEQ ID NO: 7, wherein the at least one polypeptide sequence comprises SEQ ID NO: 21. In some aspects, the present disclosure provides a binding molecule comprising at least one polypeptide sequence with at least about 94% sequence identity to SEQ ID NO: 7, wherein the at least one polypeptide sequence comprises SEQ ID NO: 21. In some aspects, the present disclosure provides a binding molecule comprising at least one polypeptide sequence with at least about 93% sequence identity to SEQ ID NO: 7, wherein the at least one polypeptide sequence comprises SEQ ID NO: 21. In some aspects, the present disclosure provides a binding molecule comprising at least one polypeptide sequence with at least about 92% sequence identity to SEQ ID NO: 7, wherein the at least one polypeptide sequence comprises SEQ ID NO: 21. In some aspects, the present disclosure provides a binding molecule comprising at least one polypeptide sequence with at least about 91% sequence identity to SEQ ID NO: 7, wherein the at least one polypeptide sequence comprises SEQ ID NO: 21. In some aspects, the present disclosure provides a binding molecule comprising at least one polypeptide sequence with at least about 90% sequence identity to SEQ ID NO: 7, wherein the at least one polypeptide sequence comprises SEQ ID NO: 21.

In some aspects, the present disclosure provides a binding molecule comprising at least one polypeptide sequence with at least about 99% sequence identity to SEQ ID NO: 8, wherein the at least one polypeptide sequence comprises SEQ ID NO: 21. In some aspects, the present disclosure provides a binding molecule comprising at least one polypeptide sequence with at least about 98% sequence identity to SEQ ID NO: 8, wherein the at least one polypeptide sequence comprises SEQ ID NO: 21. In some aspects, the present disclosure provides a binding molecule comprising at least one polypeptide sequence with at least about 97% sequence identity to SEQ ID NO: 8, wherein the at least one polypeptide sequence comprises SEQ ID NO: 21. In some aspects, the present disclosure provides a binding molecule comprising at least one polypeptide sequence with at least about 96% sequence identity to SEQ ID NO: 8, wherein the at least one polypeptide sequence comprises SEQ ID NO: 21. In some aspects, the present disclosure provides a binding molecule comprising at least one polypeptide sequence with at least about 95% sequence identity to SEQ ID NO: 8, wherein the at least one polypeptide sequence comprises SEQ ID NO: 21. In some aspects, the present disclosure provides a binding molecule comprising at least one polypeptide sequence with at least about 94% sequence identity to SEQ ID NO: 8, wherein the at least one polypeptide sequence comprises SEQ ID NO: 21. In some aspects, the present disclosure provides a binding molecule comprising at least one polypeptide sequence with at least about 93% sequence identity to SEQ ID NO: 8, wherein the at least one polypeptide sequence comprises SEQ ID NO: 21. In some aspects, the present disclosure provides a binding molecule comprising at least one polypeptide sequence with at least about 92% sequence identity to SEQ ID NO: 8, wherein the at least one polypeptide sequence comprises SEQ ID NO: 21. In some aspects, the present disclosure provides a binding molecule comprising at least one polypeptide sequence with at least about 91% sequence identity to SEQ ID NO: 8, wherein the at least one polypeptide sequence comprises SEQ ID NO: 21. In some aspects, the present disclosure provides a binding molecule comprising at least one polypeptide sequence with at least about 90% sequence identity to SEQ ID NO: 8, wherein the at least one polypeptide sequence comprises SEQ ID NO: 21.

In some aspects, any binding molecule of the present disclosure can exhibit reduced background reactivity in an immunogenicity (ADA) assay compared to a binding molecule comprising a CH sequence comprising SEQ ID NO: 3. In some aspects, any binding molecule of the present disclosure can exhibit reduced background reactivity in an immunogenicity (ADA) assay compared to a binding molecule comprising a CH sequence comprising SEQ ID NO: 4.

Therapeutic Administration and Formulations

The disclosure provides therapeutic compositions comprising the anti-IL-4Rα binding molecules of the present disclosure. The administration of therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the binding molecule of the present disclosure is used for treating various conditions and diseases associated with IL-4Rα, in an adult patient, it is advantageous to intravenously administer the binding molecule of the present disclosure normally at a single dose of about 0.01 to about 20 mg/kg body weight, more typically about 0.02 to about 7, about 0.03 to about 5, or about 0.05 to about 3 mg/kg body weight. In some aspects, when the binding molecule of the present disclosure is used for treating various conditions and diseases associated with IL-4Rα, the dosing regimen can be 300 mg once every two weeks (Q2W) and can be extended up to every four weeks (Q4W). Depending on the severity of the condition, the frequency and the duration of the treatment can be adjusted.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, for example a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327.

In certain embodiments, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used (see Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984). Other controlled release systems are discussed in the review by Langer (1990) Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid binding molecule contained is generally about 5 to 500 mg per dosage form in a unit dose; especially in the form of injection, in certain embodiments the aforesaid binding molecule is contained in about 5 to 100 mg and in about 10 to 250 mg for the other dosage forms.

Single and combination therapies. The binding molecules of the disclosure are useful for treating diseases and disorders which are improved, inhibited or ameliorated by reducing IL-4 activity. These disorders include those characterized by abnormal or excess expression of IL-4, or by an abnormal host response to IL-4 production.

The disclosure encompasses combination therapies in which the anti-IL-4Rα binding molecule (e.g., antibody or antibody fragment) is administered in combination with a second therapeutic agent. Co-administration and combination therapy are not limited to simultaneous administration, but include treatment regimens in which an anti-IL-4Rα binding molecule is administered at least once during a course of treatment that involves administering at least one other therapeutic agent to the patient. A second therapeutic agent may be another IL-4 antagonist, such as another binding molecule, or a soluble cytokine receptor, an IgE antagonist, an anti-asthma medication (corticosteroids, nonsteroidal agents, β-agonists, leukotriene antagonists, xanthines, fluticasone, salmeterol, albuterol) which may be delivered by inhalation or other appropriate means. In a specific embodiment, the anti-IL-4Rα binding molecule such as a binding molecule of the disclosure may be administered with an IL-1 antagonist, such as rilonacept, or an IL-13 antagonist. In some aspects, an anti-IL-4Rα binding molecule such as a binding molecule of the present disclosure may be administered in combination with a binding molecule that target cytokines and/or receptors in the Type 1 or Type 2 inflammatory response. The second agent may include one or more leukotriene receptor antagonists to treat disorders such as allergic inflammatory diseases, e.g., asthma and allergies. Examples of leukotriene receptor antagonists include but are not limited to montelukast, pranlukast, and zafirlukast. The second agent may include a cytokine inhibitor such as one or more of a TNF (etanercept, ENBREL™), IL-9, IL-5 or IL-17 antagonist.

Therapeutic Uses

The disclosure provides compositions and methods for treating a disease or disorder in a subject in need thereof, comprising administering to the subject a therapeutically effective amount of a binding molecule of the present disclosure.

The disclosure provides compositions and methods for treating a disease or disorder in a subject in need thereof, comprising administering to the subject a therapeutically effective amount of a composition of the disclosure.

In certain embodiments of the present disclosure, the disease or disorder is an Type 1 or Type 2 inflammatory disease or disorder.

In certain embodiments of the instant disclosure, the disease or disorder is an autoimmune disease or disorder.

In certain embodiments of the present disclosure, the disease or disorder is an allergic disease or disorder.

In certain embodiments of the disclosure, the disease or disorder is an immune disease or disorder.

In certain embodiments of the instant disclosure, the disease or disorder is a benign proliferative disease or disorder. In certain embodiments of the instant disclosure, the disease or disorder is a malignant proliferative disease or disorder.

In certain embodiments of the present disclosure, the disease or disorder is atopic dermatitis, asthma, allergic rhinitis, allergic conjunctivitis, eosinophilic esophagitis, nasal polyps or a combination thereof.

In certain embodiments of the disclosure, a binding molecule of the present invention is administered systemically. In one aspect, the binding molecule is administered intravenously or subcutaneously. In another aspect, the binding molecule is administered by an injection or an infusion. In still another aspect, the binding molecule is administered by a subcutaneous injection.

In certain embodiments of the present disclosure, the binding molecule is administered systemically. In one aspect, the binding molecule is administered by a subcutaneous injection. In another aspect, a therapeutically effective dose comprises a subcutaneous injection of about 75 mg, 150 mg, 300 mg or 600 mg. In yet another aspect, the therapeutically effective dose comprises at least one subcutaneous injection, at least two subcutaneous injections, at least three subcutaneous injections, or at least four subcutaneous injections of about 75 mg, 150 mg, 300 mg or 600 mg. In still another aspect, the therapeutically effective dose comprises a subcutaneous injection of about 75 mg, 150 mg, 300 mg or 600 mg once every week, once every two weeks, once every four weeks or chronically administered as a maintenance dose to control disease symptoms.

In certain embodiments of the disclosure, the binding molecule is administered systemically. In one aspect, the binding molecule is administered by a subcutaneous injection. In another aspect, the therapeutically effective dose comprises an initial dose of about 600 mg. In still another aspect, the initial dose comprises a pair of injections of 300 mg each, administered at two distinct injection sites. In yet another aspect, including those wherein the therapeutically effective dose comprises an initial dose, the therapeutically effective dose further comprises a maintenance dose of about 300 mg. In another aspect, maintenance dose is administered every other week.

In certain embodiments of the methods of the disclosure, the binding molecule is administered systemically. In one aspect, the binding molecule is administered intravenously at a dose of about 1.0 mg/kg, 3.0 mg/kg, 8.0 mg/kg, or 12.0 mg/kg.

In certain embodiments of the disclosure, the binding molecule is administered in combination with a second therapeutic agent. In one aspect, the second therapeutic agent comprises an immunosuppressant. In one aspect, the second therapeutic agent comprises an agonistic antibody. In one aspect, the second therapeutic agent comprises an immunoactivator. In another aspect, the second therapeutic agent comprises an IL-1 β-inhibitor, an IL-5 inhibitor, an IL-9 inhibitor, an IL-3 inhibitor, an IL-13 inhibitor, an IL-17 inhibitor, an IL-25 inhibitor, a TNFα inhibitor, an eotixin-3 inhibitor, an IgE inhibitor, a prostaglandin D2 inhibitor, an immunosuppressant, a corticosteroid, a glucocorticoid, a proton pump inhibitor, a non-steroidal anti-inflammatory drug (NSAID), or a combination thereof.

In certain embodiments of the disclosure, the binding molecule is administered in combination with a second therapeutic agent. In one aspect, the second therapeutic agent comprises a corticosteroid. In a particular aspect, the corticosteroid is a topical corticosteroid.

It should be appreciated that the compositions, formulations, kits, methods of the present disclosure is not limited to any one disease and/or medical condition. The compositions, formulations, kits and methods of the present disclosure can be applied to any disease and/or medical condition in which a patient exhibits pre-existing reactivity to therapeutic antibodies.

TABLE 1

Exemplary sequences of the disclosure.

| Name | Sequence | SEQ ID NO: |
|---|---|---|
| IgG4 $C_H1$ | ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRV | 1 |
| IgG4 $C_H2$ | APEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPS SIEKTISKAK | 2 |

TABLE 1-continued

Exemplary sequences of the disclosure.

| Name | Sequence | SEQ ID NO: |
|---|---|---|
| IgG4 $C_H3$ | GQPREPQVYTLPPSQEEMTKNQVSLTCLVKGFYPSDIAVEW ESNGQPENNYKTTPPVLDSDGSFFLYSRLTVDKSRWQEGNV FSCSVMHEALHNHYTQKSLSLSLGK | 3 |
| IgG4 $C_H$ | ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKY GPPCPSCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSC SVMHEALHNHYTQKSLSLSLGK | 4 |
| IgG1 $C_H3$ | GQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLS LSPGK | 5 |
| IgG2 $C_H3$ | GQPREPQVYTLPPSREEMTKNQVSLTCLVKGFYPSDISVEWESNGQPENNY KTTPPMLDSDGSFFLYSKLTVDKSRWQQGNVFSCSVMHEALHNHYTQKSL SLSPGK | 6 |
| IgG4 $C_H3$ L > P | GQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLS LSPGK | 7 |
| IgG4 $C_H$ L > P | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPSCPAPEFLGGPSVFLFPPKPKDTLMISRTPEVTCVVVDVSQEDPEVQFNW YVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHE ALHNHYTQKSLSLSPGK | 8 |
| Heavy Chain CDR1 | GFTFRDYA | 9 |
| Heavy Chain CDR2 | ISGSGGNT | 10 |
| Heavy Chain CDR3 | AKDRLSITIRPRYYGL | 11 |
| Light Chain CDR1 | QSLLYSIGYNY | 12 |
| Light Chain CDR2 | LGS | NA |
| Light Chain CDR3 | MQALQTPYT | 14 |
| Heavy chain variable region | EVQLVESGGGLEQPGGSLRLSCAGSGFTFRDYAMTWVRQAPGKGLEWVSSI SGSGGNTYYADSVKGRFTISRDNSKNTLYLQMNSLRAEDTAVYYCAKDRL SITIRPRYYGLDVWGQGTTVTVS | 15 |
| Light chain variable region | DIVMTQSPLSLPVTPGEPASISCRSSQSLLYSIGYNYLDWYLQKSGQSPQLLI YLGSNRASGVPDRFSGSGSGTDFTLKISRVEAEDVGFYYCMQALQTPYTFG QGTKLEIK | 16 |
| Hinge region of IgG4 $C_H2$ | APEFLG | 17 |
| IL4Rα | MKVLQEPTCVSDYMSISTCEWKMNGPTNCSTELRLLYQLVFLLSEAHTCIPE NNGGAGCVCHLLMDDVVSADNYTLDLWAGQQLLWKGSFKPSEHVKPRAP GNLTVHTNVSDTLLLTWSNPYPPDNYLYNHLTYAVNIWSENDPADFRIYNV TYLEPSLRIAASTLKSGISYRARVRAWAQCYNTTWSEWSPSTKWHNSYREP FEQH | 18 |

TABLE 1-continued

Exemplary sequences of the disclosure.

| Name | Sequence | SEQ ID NO: |
|---|---|---|
| IgG1 $C_H$ | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSD IAVEWESNGQPENNYKTTPPVLDSDGSFFLYSKLTVDKSRWQQGNVFSCSV MHEALHNHYTQKSLSLSPGK | 19 |
| IgG4 $C_H$ | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPPCPAPEFLGGPSVFLFPPKPKDTLMISRTPEVTCVVVDVSQEDPEVQFNW YVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHE ALHNHYTQKSLSLSLGK | 20 |
| IgG4 region of $C_H3$ | LSPG | 21 |
| truncated IgG4 $C_H$ | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPSCPAPEFLGGPSVFLFPPKPKDTLMISRTPEVTCVVVDVSQEDPEVQFNW YVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHE ALHNHYTQKSLSLS | 22 |
| IgG2 $C_H$ | ASTKGPSVFPLAPCSRSTSESTAALGCLVKDYFPEPVTVSWNSGALTSGVHT FPAVLQSSGLYSLSSVVTVPSSNFGTQTYTCNVDHKPSNTKVDKTVERKCC VECPPCPAPPVAGPSVFLFPPKPKDTLMISRTPEVTCVVVDVSHEDPEVQFN WYVDGVEVHNAKTKPREEQFNSTFRVVSVLTVVHQDWLNGKEYKCKVSN KGLPAPIEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVM HEALHNHYTQKSLSLSPGK | 23 |
| truncated IgG4 $C_H3$ | GQPREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQKSLS LS | 13 |

EXAMPLES

Example 1: Replacement of the IgG4 $C_H3$ Constant Regions Reduces Pre-Existing Immunoreactivity in Some Patient Samples Competitive inhibition studies were conducted to characterize the high pre-existing reactivity signals observed in some samples. Antibody reagents commercially obtained or monoclonal antibodies specifically constructed for this purpose were used in these studies. A list antibody constructs or reagents that helped elucidate the specificity of this pre-existing reactivity is provided in Table 2.

TABLE 2

| Antibody/Reagent Name | Isotype | Properties |
|---|---|---|
| Fc Hinge Region Constructs | | |
| Dupilumab | IgG4κ | CPPC (Fc hinge sequence) |
| REGN-A | IgG4κ | CPPC (Fc hinge sequence) not specific to IL-4R |
| REGN-B, C and E | IgG4κ | CPPC (Fc hinge sequence) |
| Commercial IgG4 wild type (WT) | IgG4κ | CPSC (Fc hinge sequence) wt IgG4 Fc |

TABLE 2-continued

| Antibody/Reagent Name | Isotype | Properties |
|---|---|---|
| Commercially Available Isotype Antibodies | | |
| Human IgG1 | IgG1κ | |
| Human IgG2 | IgG2λ | |
| Human IgG3 | IgG3κ | |
| Dupilumab & Bioengineered Antibodies | | |
| REGN-D (Dupilumab) | IgG4κ | CPPC (Fc hinge sequence) |
| REGN-B | IgG4κ | $C_H2$-IgG4-$C_H3$-IgG1 |
| REGN-C | IgG4κ | $C_H2$-IgG4-$C_H3$ L445 > P |
| REGN-E | IgG4κ | $C_H2$-IgG4-$C_H3$ truncated @ 444 |

These antibody constructs were used at 200 μg/mL as competitive inhibitors in the anti-drug antibody (ADA) confirmation assay format. The format of the assay is shown in FIG. 4 and the results of the assay are shown in FIG. 1 (FIG. 1 and FIG. 4). High percent inhibition in the assay indicates that the given competitor was able to inhibit the pre-existing reactivity signals in these samples, suggesting that the competitor molecule contains a region to which the pre-existing reactivity binds. Lower percent inhibitions indicate that the competitor molecule does not contain a region to which the pre-existing reactivity can bind. The reagents listed in Table 1 above can be broadly grouped into three categories, IgG4 backbone/Fc Hinge region constructs, commercially available isotype antibodies and dupilumab bioengineered constructs. Initial experiments examined whether this high assay reactivity was directed towards the CDR or the IgG4 backbone of dupilumab. REGN-A is a human monoclonal antibody that has the same IgG4 backbone as dupilumab, but a different CDR sequence and it does not bind to IL-4Rα.

As shown in FIG. 1, competitive inhibition experiments using both dupilumab and REGN-A demonstrated significant inhibition of the high assay signals in the six baseline samples from the patients examined. As the CDR region sequences of these two antibodies are different, this inhibition result suggests that the high signal reactivity is not targeted to the CDR portion of dupilumab but rather to some common antibody backbone sequences. Both dupilumab and REGN-A contain an IgG1 "CPPC" hinge region sequence that stabilizes the antibody hinge region in these IgG4 molecules. In order to determine if the pre-existing immunoreactivity is targeting this CPPC mutation, a commercial IgG4κ antibody which has the wild type (wt) CPSC sequence at the hinge region was examined in the competitive inhibition experiment. As can be seen in FIG. 1, the wild type IgG4 antibody also showed significant inhibition similar to dupilumab and REGN-A. This result suggests that the high baseline assay signal is not directed to the CPPC hinge region mutation in dupilumab but is most likely directed against the wild type constant regions of the IgG4 molecule. These results indicate that the high signals observed at baseline are not specific to dupilumab.

Additional experiments were conducted to determine whether this high assay pre-existing reactivity was directed towards the constant region sequences that would be common amongst the different IgG subtypes. Using the same competitive inhibition approach, the impact of three commercially obtained human IgG1κ, IgG2κ, IgG3κ antibodies on this pre-existing response was examined. None of these antibodies inhibited the high baseline signals in these samples (See FIG. 1). This suggested that the pre-existing reactivity was most likely associated with a region that is unique to the IgG4 constant region sequences and that was not shared by any of the IgG subtypes tested.

Figure 2:
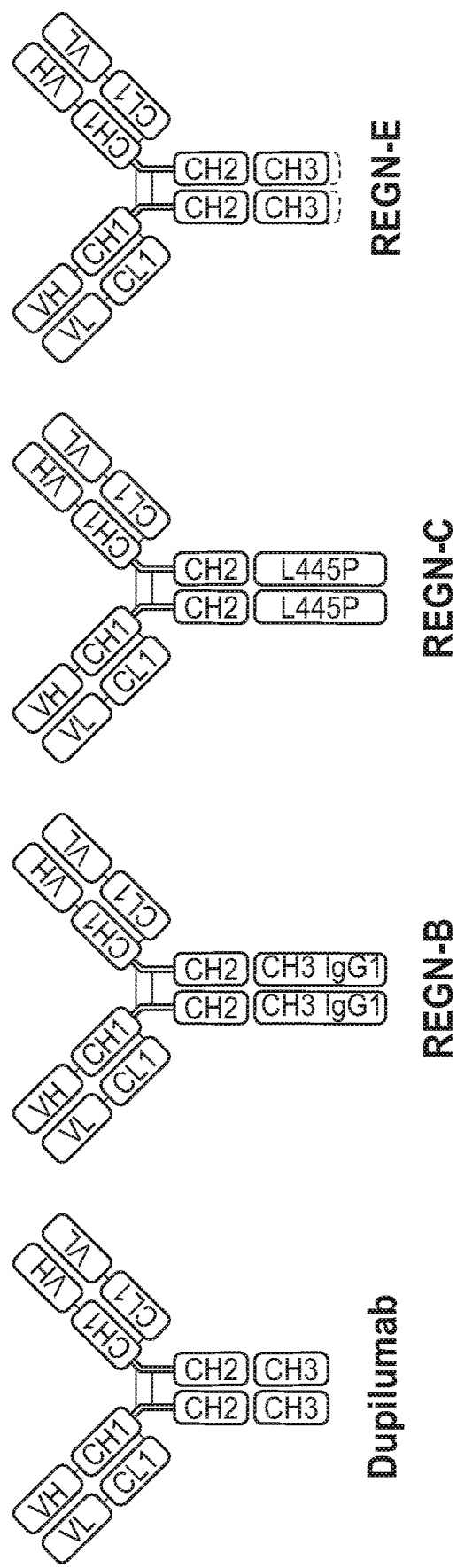
FIG. 2 is a drawing showing a diagrammatic representation of the three key constructs and their structural differences in comparison to dupilumab. REGN-B, REGN-C and REGN-E are molecular analogues of dupilumab. All three constructs are IgG4k constructs that have the same specificity and similar affinity for anti-IL4R as dupilumab and also possess the same CPPC hinge region mutation sequence present in dupilumab.

A human monoclonal antibody (REGN-B) was constructed which was similar to dupilumab except that the IgG4 $C_H3$ domain was replaced by an IgG1 $C_H3$ domain (See FIG. 2). This antibody was examined in the competition studies to determine if the pre-existing reactivity was targeted to the $C_H3$ domain of dupilumab. REGN-B did not significantly inhibit the high signals in the samples (see FIG. 1), suggesting that the pre-existing reactivity is most likely targeting some region within the $C_H3$ domain of the IgG4 molecule.

To further identify the area that may be associated with these high signals within the $C_H3$ domain of dupilumab, an amino acid sequence alignment of the $C_H3$ domain of IgG4, IgG1 and IgG2 antibodies was conducted (see FIG. 3). Differences at six individual amino acid positions between the IgG4 and IgG1 $C_H3$ domain sequences and five individual amino acid positions between the IgG4 and IgG2 $C_H3$ domain sequences were noted (See FIG. 3).

In IgG4 construct with a leucine (L) to proline (P) substitution at position 445 was available and was examined in the competitive inhibition assay. This construct did not show significant inhibition of these high assay signals. This indicated that the pre-existing reactivity was probably specific to the L445 region of dupilumab. Additional samples with high assay signal were examined in the competitive inhibition assay using this construct with L to P substitution at position 445 and similar low levels of inhibition were observed. This appeared to confirm that the pre-existing reactivity is specifically targeting the region around L445. Therefore a change from Leucine (in wt IgG4) to Proline (present at the same position in wt IgG1, IgG2 and IgG3) in dupilumab abrogates this pre-existing response that leads to the high signals in the ADA assay.

An IgG4 construct with a leucine (L) to proline (P) substitution at position 445 was available and was examined in the competitive inhibition assay. This construct did not show significant inhibition of these high assay signals. This indicated that the pre-existing reactivity was probably specific to the L445 region of dupilumab. Additional samples with high assay signal were examined in the competitive inhibition assay using this construct with L to P substitution at position 445 and similar low levels of inhibition were observed. This appeared to confirm that the pre-existing reactivity is specifically targeting the region around L445. Therefore a change from Leucine (in wt IgG4) to Proline (present at the same position in wt IgG1, IgG2 and IgG3) in dupilumab abrogates this pre-existing response that leads to the high signals in the ADA assay.

A second dupilumab based human monoclonal antibody construct (REGN-C), was generated. This construct is identical to dupilumab except for the insertion of a point mutation at the 445 residue in the antibody sequence, where a Leucine is changed to Proline (abbreviated as L>P). REGN-C could not significantly inhibit the high signals in the baseline samples that were tested (see FIG. 1 and FIG. 2). This confirmed that the pre-existing reactivity is specifically targeting the region around L445 in dupilumab and suggested that using this bioengineered dupilumab in the ADA assay eliminates most if not all of the high level background signal observed in the current ADA assay.

Figure 7:
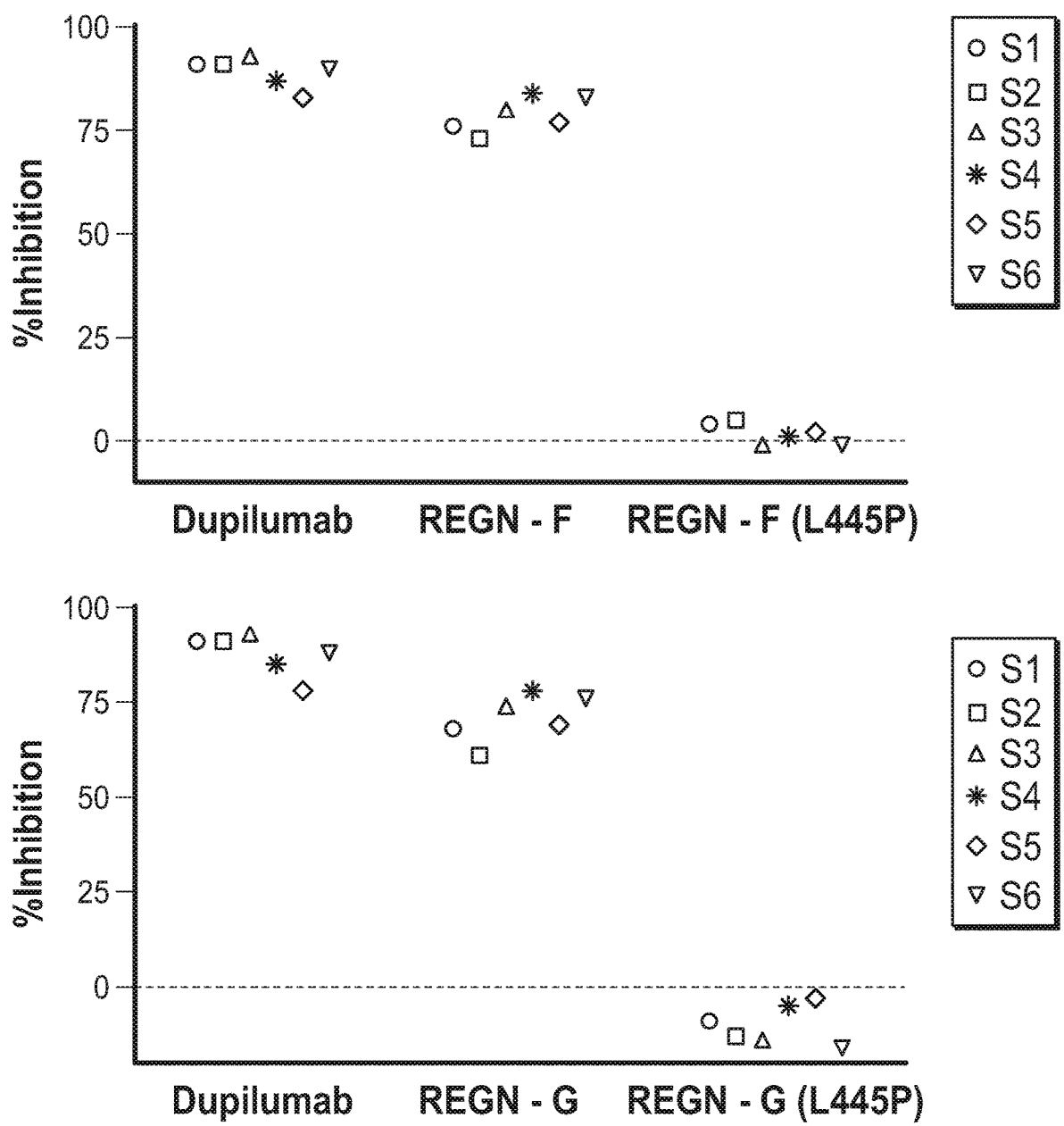
FIG. 7 is a series of plots characterizing the specificity of pre-existing reactivity in baseline patient samples using competitive antibody constructs in an anti-drug antibody (ADA) assay. On the y-axis, percent inhibition from 0 to 100 in increments of 25. On the X-axis, the specific competitive antibody construct used in the bridging assay, listed from left to right: dupilumab, REGN-F and REGN-F (L445P) in the top plot or dupilumab, REGN-G and REGN-G (L445P) in the bottom plot. The six patient samples (S1-S6) are represented, in order, as a circle, a square, a triangle point up, an asterisk, a diamond, and a triangle point down. Antibody reagents mentioned in the graph were used at 200 µg/mL as competitive inhibitors in the ADA confirmation assay format. High percent inhibition in the assay indicates that the given competitor was able to inhibit the pre-existing signals in these samples, suggesting that the competitor molecule contains a region to which the pre-existing reactivity binds. Lower percent inhibitions indicate that the competitor molecule does not contain a region to which the pre-existing reactivity can bind.
Figure 8:
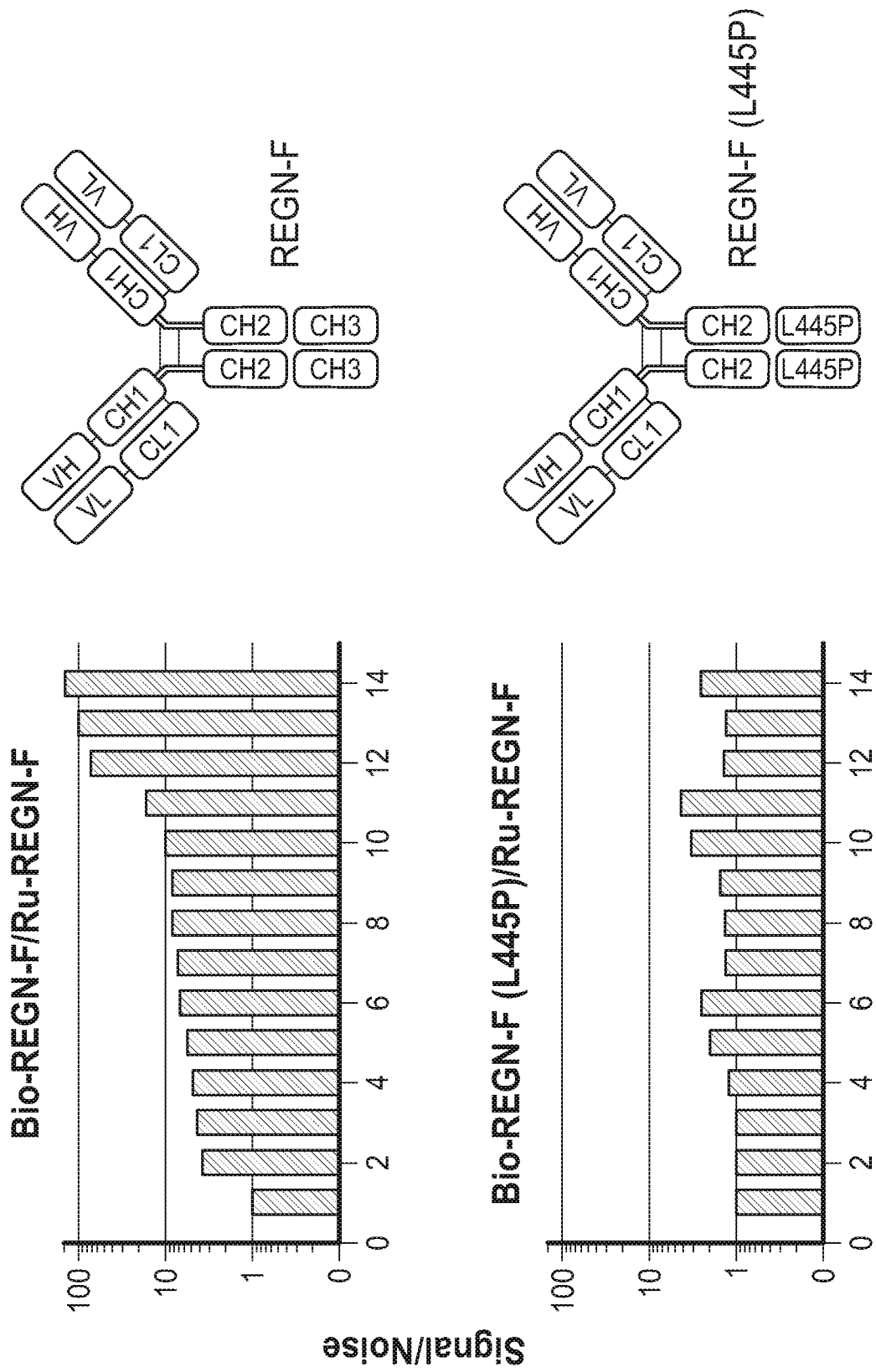
FIG. 8 is a series of plots showing assay signal from a subset of patient baseline samples using a drug specific bridging anti-drug antibody (ADA) assay, similar to that described in FIG. 4, with either REGN-F used both as the capture and detection reagents (top) or with REGN-F (L445P) used as the capture reagent in combination with REGN-F as the detection reagent.
Figure 9:
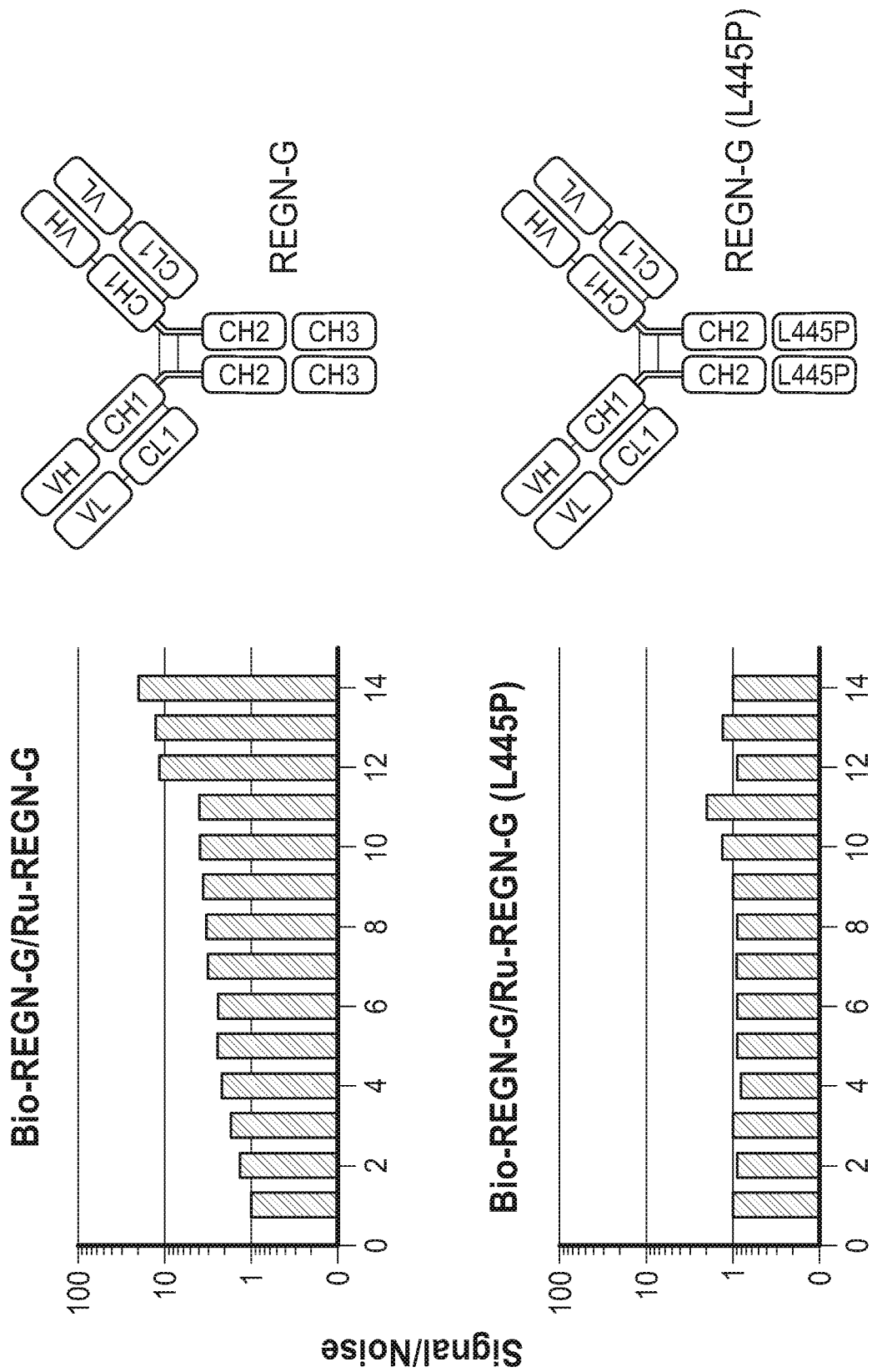
FIG. 9 is a series of plots showing assay signal from a subset of patient baseline samples using a drug specific bridging anti-drug antibody (ADA) assay, similar to that described in FIG. 4, with either REGN-G used both as the capture and detection reagents (top) or with REGN-G used as the capture reagent in combination with REGN-G (L445P) as the detection reagent.

Further experiments were performed using two additional antibodies, REGN-F and REGN-G, to demonstrate that the modification of the 445 residue in the antibody sequence from Leucine to Proline abrogates pre-existing reactivity. As shown in FIG. 7, competitive inhibition experiments using Dupilumab, REGN-F and REGN-G demonstrated significant inhibition of the high assay signals in the six baseline samples, thus showing the Dupilumab, REGN-F and REGN-G exhibit a high level of pre-existing reactivity. However, a substitution of Leucine for Proline at position 445 of REGN-F and REGN-G, herein referred to as REGN-F (L445P) and REGN-G (L445P) respectively, abrogated this pre-existing reactivity, as REGN-F and REGN-G were unable to inhibit the high assay signals. REGN-F, REGN-F (L445P), REGN-G and REGN-G (L445P) were also tested as reagents in a drug specific bridging anti-drug antibody assay, similar to that described in FIG. 4. As shown in FIGS. 8 and 9, when REGN-F and REGN-G were used both as the capture and detection reagents demonstrated high assay signal indicative of high pre-existing reactivity. In contrast, when REGN-F (L445P) was used as the capture reagent in combination with REGN-F as the detection reagent (FIG. 8), or when REGN-G was used as the capture reagent in combination with REGN-G (L445P) as the detection reagent (FIG. 9), the assay signal was significantly reduced, demonstrating that the L445P substitutions abrogate the pre-existing reactivity. REGN-F and REGN-G comprise distinct variable domains which are also different from the variable domains of the antibodies tested in the results shown in FIG. 1. Thus, the results shown in FIGS. 7-9 demonstrate that the pre-existing reactivity is independent of the variable domains and the CDRs, and instead is specific to the region around L445. Moreover, it demonstrates that the L445P substitution can be generally applied to IgG4 antibodies regardless of the identity of their CDRs to reduce pre-existing reactivity.

A region in the dupilumab sequence to which at least most of the pre-existing reactivity is targeted has been identified. The high signals in the ADA assay appear to have been generated due to some matrix constituent in these serum samples that can bridge between the labeled dupilumab molecules in the assay by binding at or near L445 in the $C_H3$ domain. This indicates that this pre-existing reactivity is not dupilumab drug specific but can bind to any IgG4 molecule. Furthermore, the results suggest that using this modified version of dupilumab with the L445P mutation in the ADA assay eliminates most if not all of the high level background signal.

Figure 5A:
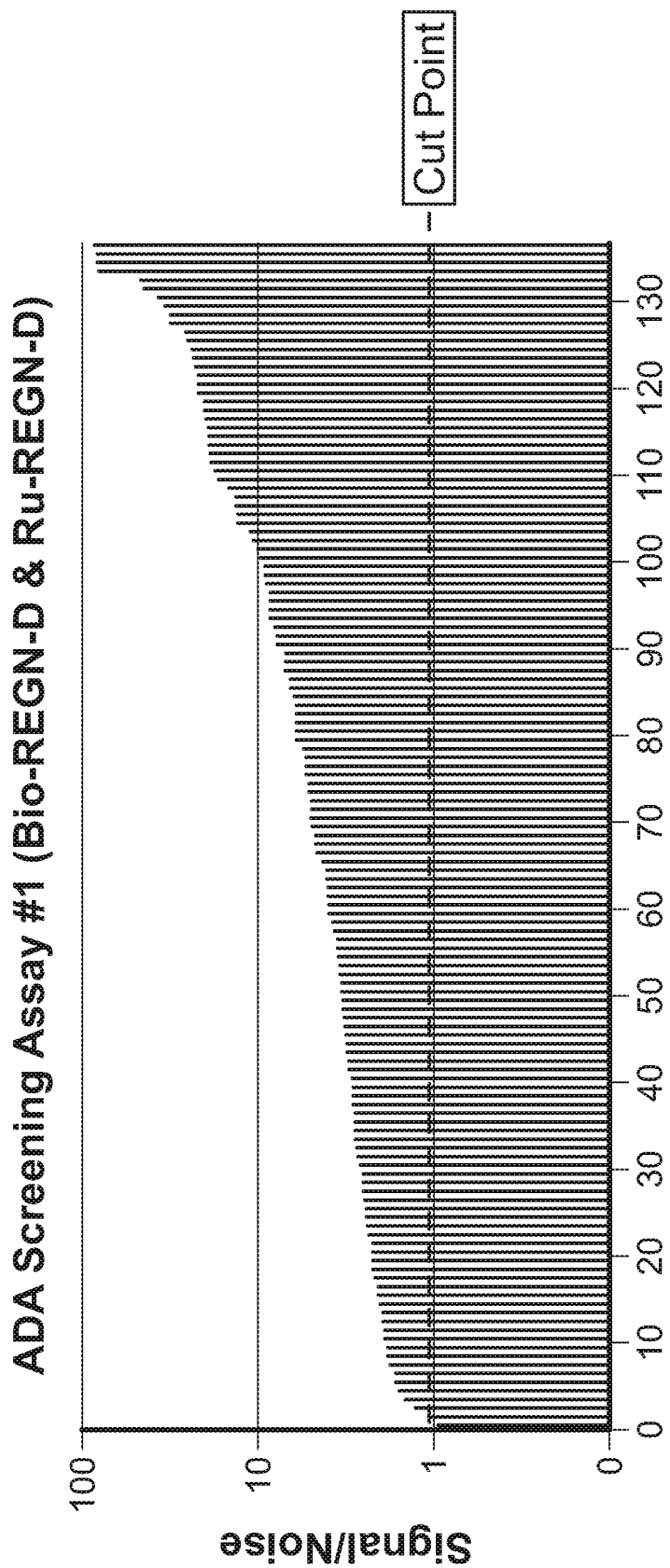
FIG. 5A is a plot showing assay signals from a subset of patient baseline samples using the original ADA assay (assay #1) which is diagrammed in panel A of FIG. 4 and uses biotinylated REGN-D as the capture agent. On the y-axis, Signal/Noise ratio in log scale from 0 to 100. On the x-axis, individual patient samples ordered by Signal/Noise ratio. The Cutpoint is given as a dashed line.
Figure 5B:
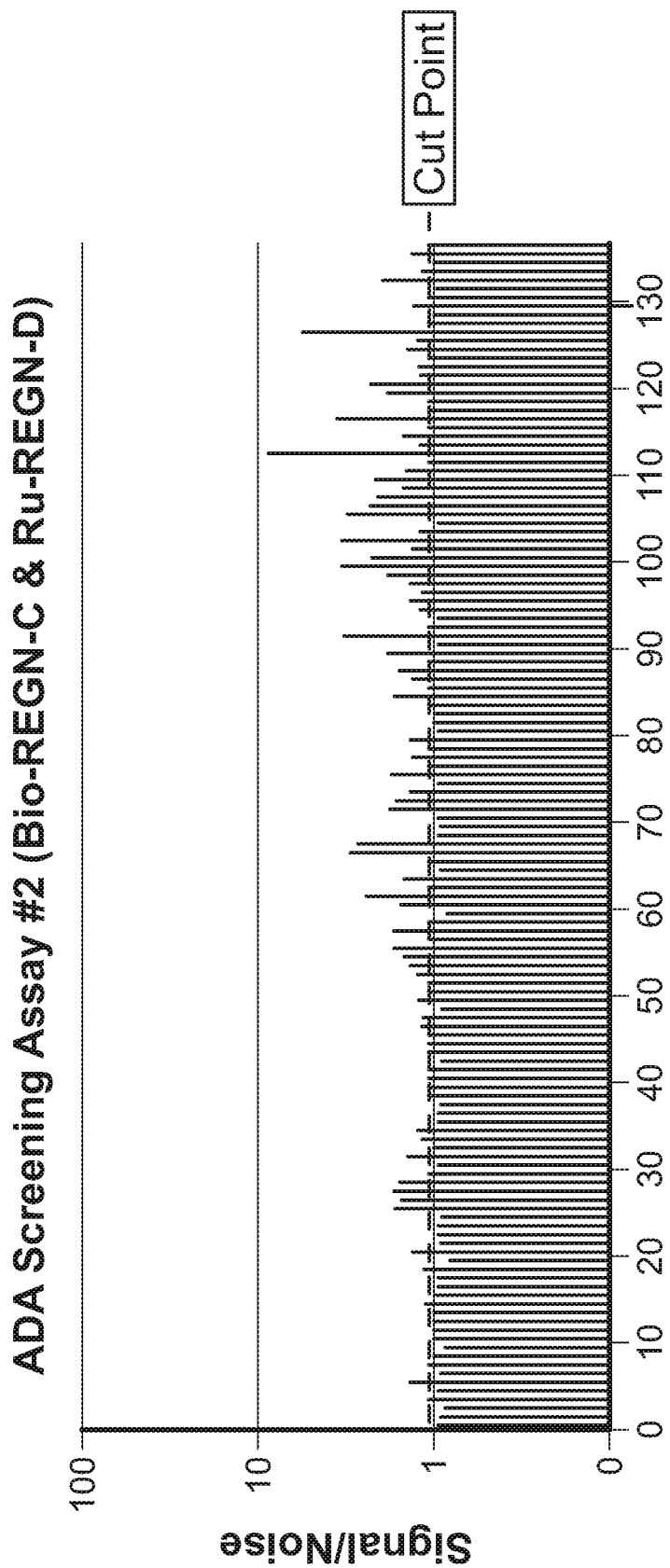
FIG. 5B is a plot showing assay signals of the same patient baseline samples using a revised ADA assay (assay #2), which is diagrammed in panel C of FIG. 4 and uses biotinylated REGN-C as the capture agent. On the y-axis, Signal/Noise ratio in log scale from 0 to 100. On the x-axis, individual patient samples in the same order as depicted in FIG. 5A. The Cutpoint is given as a dashed line.

Example 2: Development of a Modified Anti-Drug Antibody (ADA) Assay that Reduces Background Immunoreactivity in Patient Samples A modified ADA assay was developed which uses of a biotinylated REGN-C (with the L445P mutation) as the capture agent. FIG. 4 illustrates the difference in the assay design between the current ADA assay and the modified ADA assay using REGN-C. For the purpose of clarity, the current ADA assay will be considered as "ADA assay #1" and the modified ADA assay will be referred to as "ADA assay #2." FIG. 5 shows a comparative analysis of the ADA screen signals obtained using the current ADA assay #1 versus ADA Assay #2, from all the patient baseline samples. Panel 5A shows a plot of the signal to noise ratio generated by these high ADA signal baseline samples in the current ADA screen assay (Assay #1), whereas Panel 5B shows a plot of the signal to noise ratio generated by the exact same samples in the ADA Assay #2. The assay format of ADA assay #2 significantly reduces the high signals observed in the current ADA screen assay. Some samples still demonstrate reactivity in ADA assay #2, but the number of screen positives falls more in line with the expected false positive rate for a screen assay and the signal response level for those positive samples is generally much lower than that observed using the current ADA assay. The observed drop of these high assay signals to near baseline values in most cases in ADA assay #2, should allow for the improved detection of treatment emergent and drug specific ADAs in a patient population.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any disclosure disclosed or claimed herein or that it alone, or in any combination with any other reference or references, teaches, suggests or discloses any such disclosure. Further, to the extent that any meaning or definition of a term in this document conflicts with any meaning or definition of the same term in a document incorporated by reference, the meaning or definition assigned to that term in this document shall govern.

Other Embodiments

While certain embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A monoclonal antibody comprising:
   - a $V_H$ CDR1 region comprising the amino acid sequence SEQ ID NO: 9; a $V_H$ CDR2 region comprising the amino acid sequence of SEQ ID NO: 10; a $V_H$ CDR3 region comprising the amino acid sequence of SEQ ID NO: 11; a $V_L$ CDR1 region comprising the amino acid sequence of SEQ ID NO: 12; a $V_L$ CDR2 region comprising the amino acid sequence of LGS; a $V_L$ CDR3 region comprising the amino acid sequence of SEQ ID NO: 14; and
   - a C-terminal heavy chain sequence, wherein the C-terminal heavy chain sequence is SEQ ID NO: 8.

2. The antibody of claim 1, wherein the antibody comprises a heavy chain variable region comprising the amino acid sequence of SEQ ID NO: 15, and a light chain variable region comprising the amino acid sequence of SEQ ID NO: 16.

3. The antibody of claim 1, wherein said antibody mitigates high background signal during an immunogenicity analysis.

4. An assay comprising
   (a) a solid support, wherein a first component is operably-linked to the solid support;
   (b) at least one capture agent,
       wherein a second component is operably-linked to the at least one capture agent,
       wherein the capture agent comprises the antibody of claim 1, and
   (c) at least one detection agent,
       wherein a detectable label is operably-linked to the detection agent, wherein the detection agent comprises the monoclonal antibody of claim 1, and
       wherein the first component and the second component selectively bind to one another.

5. The assay of claim 4, wherein the first component comprises streptavidin and the second component comprises biotin.

6. An assay comprising
   (a) a solid support, wherein a first component is operably-linked to the solid support;
   (b) at least one capture agent, wherein a second component is operably-linked to the at least one capture agent and wherein the capture agent comprises the monoclonal antibody of claim 1; and
   (c) at least one detection agent, wherein a detectable label is operably-linked to the detection agent and wherein the detection agent comprises dupilumab;
       wherein the first component and the second component selectively bind to one another.

7. The assay of claim 6, wherein the first component comprises streptavidin and the second component comprises biotin.

8. The assay of claim 6, wherein the at least one capture agent does not bind an antibody that does not specifically bind to a sequence of a variable region of dupilumab.

9. The assay of claim 6, wherein the at least one capture agent and the at least one detection agent binds to an antibody that specifically binds to a sequence of a variable region of dupilumab.

10. A method of determining a level of immunogenicity of a monoclonal antibody therapy in a subject, comprising
    (a) contacting a biological sample from the subject with the assay of claim 4 under conditions suitable to allow binding of at least one antibody in the biological sample with the at least one capture agent and to the at least one detection agent, wherein the subject has been administered the monoclonal antibody therapy prior to the contacting step,
    (b) detecting a signal from the at least one detection agent, and
    (c) identifying the level of immunogenicity of the subject as high when the signal from (b) is above a threshold value or
    (d) identifying the level of immunogenicity of the subject as low when the signal from (b) is below the threshold value.

11. The method of claim 10, wherein the monoclonal antibody therapy comprises an antibody comprising a C-terminal heavy chain sequence comprising a sequence selected from the group consisting of SEQ ID NO: 7 and SEQ ID NO: 13.

12. The method of claim 10, wherein the monoclonal antibody therapy comprises dupilumab.

13. The method of claim 10, wherein the threshold is a predetermined value or a safety threshold.

14. The method of claim 10, wherein the monoclonal antibody therapy is beginning and the level of immunogenicity is a baseline level.

15. The method of claim 10, wherein the monoclonal antibody therapy is ongoing and the level of immunogenicity is a subsequent level.

16. The method of claim 10, wherein the monoclonal antibody therapy is ending and the level of immunogenicity is a final level.

17. The method of claim 10, wherein the subject has an inflammatory disease or disorder, an autoimmune disease or disorder, an allergic disease or disorder, an immune disease or disorder, a benign proliferative disease or disorder, atopic dermatitis, asthma, allergic rhinitis, allergic conjunctivitis, eosinophilic esophagitis, nasal polyps or any combination thereof.

* * * * *

SEQUENCE LISTING

```
<160> NUMBER OF SEQ ID NOS: 26

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 2
<211> LENGTH: 110
```

<212> TYPE: PRT
<213> ORGANISM: Homo sapiens

<400> SEQUENCE: 2

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 3
<211> LENGTH: 107
<212> TYPE: PRT
<213> ORGANISM: Homo sapiens

<400> SEQUENCE: 3

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys

```
                     85                  90                  95
Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 107
<212> TYPE: PRT
<213> ORGANISM: Homo sapiens

<400> SEQUENCE: 5

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 6
<211> LENGTH: 107
```

```
<212> TYPE: PRT
<213> ORGANISM: Homo sapiens

<400> SEQUENCE: 6

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ser Val Glu Trp Glu Ser Asn Gly Gln Pro Glu
            35                  40                  45

Asn Asn Tyr Lys Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 107
<212> TYPE: PRT
<213> ORGANISM: Homo sapiens

<400> SEQUENCE: 7

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 8
<211> LENGTH: 327
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

```
                85                  90                  95
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 9
<211> LENGTH: 8
<212> TYPE: PRT
<213> ORGANISM: Artificial Sequence
<220> FEATURE:
<223> OTHER INFORMATION: Heavy Chain CDR1

<400> SEQUENCE: 9

Gly Phe Thr Phe Arg Asp Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Heavy Chain CDR2

<400> SEQUENCE: 10

Ile Ser Gly Ser Gly Gly Asn Thr
1               5

<210> SEQ ID NO 11
<211> LENGTH: 16
<212> TYPE: PRT
<213> ORGANISM: Artificial Sequence
<220> FEATURE:
```

<223> OTHER INFORMATION: Heavy Chain CDR3

<400> SEQUENCE: 11

Ala Lys Asp Arg Leu Ser Ile Thr Ile Arg Pro Arg Tyr Tyr Gly Leu
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Light Chain CDR1

<400> SEQUENCE: 12

Gln Ser Leu Leu Tyr Ser Ile Gly Tyr Asn Tyr
1               5                   10

<210> SEQ ID NO 13
<211> LENGTH: 104
<212> TYPE: PRT
<213> ORGANISM: Homo sapiens

<400> SEQUENCE: 13

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser
            100

<210> SEQ ID NO 14
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 14

Met Gln Ala Leu Gln Thr Pro Tyr Thr
1               5

<210> SEQ ID NO 15
<211> LENGTH: 124
<212> TYPE: PRT
<213> ORGANISM: Homo sapiens

<400> SEQUENCE: 15

Glu Val Gln Leu Val Glu Ser Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

```
Ser Ser Ile Ser Gly Ser Gly Gly Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
                100                 105                 110

Asp Val Trp Gly Gln Gly Thr Thr Val Thr Val Ser
                115                 120

<210> SEQ ID NO 16
<211> LENGTH: 112
<212> TYPE: PRT
<213> ORGANISM: Homo sapiens

<400> SEQUENCE: 16

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Tyr Ser
                 20                  25                  30

Ile Gly Tyr Asn Tyr Leu Asp Trp Tyr Leu Gln Lys Ser Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Ala
                 85                  90                  95

Leu Gln Thr Pro Tyr Thr Phe Gly Gln Gly Thr Lys Leu Glu Ile Lys
                100                 105                 110

<210> SEQ ID NO 17
<211> LENGTH: 6
<212> TYPE: PRT
<213> ORGANISM: Homo sapiens

<400> SEQUENCE: 17

Ala Pro Glu Phe Leu Gly
  1               5

<210> SEQ ID NO 18
<211> LENGTH: 207
<212> TYPE: PRT
<213> ORGANISM: Homo sapiens

<400> SEQUENCE: 18

Met Lys Val Leu Gln Glu Pro Thr Cys Val Ser Asp Tyr Met Ser Ile
  1               5                  10                  15

Ser Thr Cys Glu Trp Lys Met Asn Gly Pro Thr Asn Cys Ser Thr Glu
                 20                  25                  30

Leu Arg Leu Leu Tyr Gln Leu Val Phe Leu Leu Ser Glu Ala His Thr
             35                  40                  45

Cys Ile Pro Glu Asn Asn Gly Gly Ala Gly Cys Val Cys His Leu Leu
         50                  55                  60

Met Asp Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
```

```
                85                  90                  95
Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
        130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
            195                 200                 205

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 20
<211> LENGTH: 327
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 21
<211> LENGTH: 4
<212> TYPE: PRT
<213> ORGANISM: Homo sapiens

<400> SEQUENCE: 21

Leu Ser Pro Gly
1

<210> SEQ ID NO 22
<211> LENGTH: 324
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

-continued

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser

<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 24
<211> LENGTH: 120
<212> TYPE: PRT
<213> ORGANISM: Homo sapiens

<400> SEQUENCE: 24

```
Leu Pro Ala Pro Ile Glu Lys Thr Ile Ser Lys Ala Lys Gly Gln Pro
1               5                   10                  15

Arg Glu Pro Gln Val Tyr Thr Leu Pro Pro Ser Arg Asp Glu Leu Thr
            20                  25                  30

Lys Asn Gln Val Ser Leu Thr Cys Leu Val Lys Gly Phe Tyr Pro Ser
        35                  40                  45

Asp Ile Ala Val Glu Trp Glu Ser Asn Gly Gln Pro Glu Asn Asn Tyr
    50                  55                  60

Lys Thr Thr Pro Pro Val Leu Asp Ser Asp Gly Ser Phe Phe Leu Tyr
65                  70                  75                  80

Ser Lys Leu Thr Val Asp Lys Ser Arg Trp Gln Gln Gly Asn Val Phe
                85                  90                  95

Ser Cys Ser Val Met His Glu Ala Leu His Asn His Tyr Thr Gln Lys
            100                 105                 110

Ser Leu Ser Leu Ser Pro Gly Lys
        115                 120
```

<210> SEQ ID NO 25
<211> LENGTH: 120
<212> TYPE: PRT
<213> ORGANISM: Homo sapiens

<400> SEQUENCE: 25

```
Leu Pro Ala Pro Ile Glu Lys Thr Ile Ser Lys Thr Lys Gly Gln Pro
1               5                   10                  15

Arg Glu Pro Gln Val Tyr Thr Leu Pro Pro Ser Arg Glu Glu Met Thr
            20                  25                  30

Lys Asn Gln Val Ser Leu Thr Cys Leu Val Lys Gly Phe Tyr Pro Ser
        35                  40                  45

Asp Ile Ala Val Glu Trp Glu Ser Asn Gly Gln Pro Glu Asn Asn Tyr
    50                  55                  60

Lys Thr Thr Pro Pro Met Leu Asp Ser Asp Gly Ser Phe Phe Leu Tyr
65                  70                  75                  80

Ser Lys Leu Thr Val Asp Lys Ser Arg Trp Gln Gln Gly Asn Val Phe
                85                  90                  95

Ser Cys Ser Val Met His Glu Ala Leu His Asn His Tyr Thr Gln Lys
            100                 105                 110

Ser Leu Ser Leu Ser Pro Gly Lys
        115                 120
```

<210> SEQ ID NO 26
<211> LENGTH: 120
<212> TYPE: PRT
<213> ORGANISM: Homo sapiens

<400> SEQUENCE: 26

```
Leu Pro Ser Ser Ile Glu Lys Thr Ile Ser Lys Ala Lys Gly Gln Pro
1               5                   10                  15

Arg Glu Pro Gln Val Tyr Thr Leu Pro Pro Ser Gln Glu Glu Met Thr
            20                  25                  30
```

```
Lys Asn Gln Val Ser Leu Thr Cys Leu Val Lys Gly Phe Tyr Pro Ser
            35              40              45
Asp Ile Ala Val Glu Trp Glu Ser Asn Gly Gln Pro Glu Asn Asn Tyr
        50              55              60
Lys Thr Thr Pro Pro Val Leu Asp Ser Asp Gly Ser Phe Phe Leu Tyr
65              70              75              80
Ser Arg Leu Thr Val Asp Lys Ser Arg Trp Gln Glu Gly Asn Val Phe
                85              90              95
Ser Cys Ser Val Met His Glu Ala Leu His Asn His Tyr Thr Gln Lys
            100             105             110
Ser Leu Ser Leu Ser Leu Gly Lys
            115             120
```